(12) United States Patent
Fulbrook et al.

(10) Patent No.: US 11,058,573 B2
(45) Date of Patent: Jul. 13, 2021

(54) HEATING / COOLING BODY TREATMENT THERAPY PAD SYSTEM

(71) Applicants: Jim E. Fulbrook, Fairfax, VA (US); Susan W. Johnson, Annandale, VA (US)

(72) Inventors: Jim E. Fulbrook, Fairfax, VA (US); Susan W. Johnson, Annandale, VA (US)

( * ) Notice: Subject to any disclaimer, the term of this patent is extended or adjusted under 35 U.S.C. 154(b) by 0 days.

(21) Appl. No.: 16/888,842

(22) Filed: May 31, 2020

(65) Prior Publication Data

US 2020/0375795 A1 Dec. 3, 2020

Related U.S. Application Data

(60) Provisional application No. 62/921,096, filed on May 31, 2019.

(51) Int. Cl.
*A61F 7/02* (2006.01)
*A61F 7/00* (2006.01)

(52) U.S. Cl.
CPC ........ *A61F 7/02* (2013.01); *A61F 2007/0003* (2013.01); *A61F 2007/003* (2013.01); *A61F 2007/0004* (2013.01); *A61F 2007/0005* (2013.01); *A61F 2007/0008* (2013.01); *A61F 2007/0012* (2013.01); *A61F 2007/0014* (2013.01); *A61F 2007/0027* (2013.01); *A61F 2007/0238* (2013.01); *A61F 2007/0268* (2013.01)

(58) Field of Classification Search
CPC combination set(s) only.
See application file for complete search history.

(56) References Cited

U.S. PATENT DOCUMENTS 5,737,774 A * 4/1998 Petty-Saphon ........... A61F 7/02
2/44
5,776,088 A * 7/1998 Sereboff ................. A61F 5/028
602/18

(Continued)

FOREIGN PATENT DOCUMENTS

JP 08117265 A * 5/1996

*Primary Examiner* — Joseph A Stoklosa
*Assistant Examiner* — Adam J Avigan
(74) *Attorney, Agent, or Firm* — Invention To Patent Services; Alex Hobson

(57) ABSTRACT

A heating/cooling therapy treatment pad system incorporates a plurality of therapy pads that can be coupled together by connectors and attachments to form an integrated therapy pad assembly. The thermal pads have pouches for receiving thermal inserts that may be heated or chilled. The thermal inserts may be cylindrical in shape and there may be thermal insert gaps, or spaces between the pouches to enable better conformability of the therapy pad to a person's body, such as around the neck. The heating/cooling therapy treatment pad system may include a neck therapy pad, spine therapy pad, head and face therapy pads, shoulder therapy pad, lumbar therapy pad, armpit thermal therapy pad and a thermal therapy pad vest. The system of pads interconnect to provide tailored thermal therapy to multiple areas of a user's body and may be used to effectuate rapid cooling and in particular for those suffering from heat exhaustion.

18 Claims, 26 Drawing Sheets

(56) References Cited

U.S. PATENT DOCUMENTS

| | | | | |
|---|---|---|---|---|
| 2001/0039442 A1* | 11/2001 | Gorge | ............... | A61F 7/02 |
| | | | | 607/109 |
| 2008/0009926 A1* | 1/2008 | Russak | ............... | A61F 7/02 |
| | | | | 607/109 |
| 2011/0066218 A1* | 3/2011 | Geibel | ............... | A61F 7/02 |
| | | | | 607/112 |
| 2013/0289680 A1* | 10/2013 | Hasegawa | ............... | F28D 20/021 |
| | | | | 607/112 |
| 2016/0165992 A1* | 6/2016 | Brandt | ............... | A42C 5/04 |
| | | | | 2/171.2 |

* cited by examiner

HEATING / COOLING BODY TREATMENT THERAPY PAD SYSTEM

CROSS REFERENCE TO RELATED APPLICATIONS

This application claims the benefit of priority to U.S. patent application No. 62/921,096, filed on May 31, 2019; the entirety of which is hereby incorporated by reference herein.

BACKGROUND OF THE INVENTION

Field of the Invention

The invention relates to a system and apparatus for providing personal thermal heating/cooling as a means of physical therapy to a user onto specific areas of a body to relieve aches, pains and muscle discomfort arising from physical strains and sprains, and to counter exposure to extreme environmental conditions such as in high temperatures where cooling may prevent or mitigate a heat casualty.

Background

Problems. Heat and cool therapies are typically applied by pads that may or may not be tailored for the body region where the therapy is needed. Heat pads may be electrical, but the most common pad type has a comfortable cloth outer layer and then an internal sack filled with some type of vegetable material such as seeds or shells that are heated in a microwave oven. Depending on the volume of heating material in the pads, it can take two-to-three minutes in a microwave oven to heat the pad for use

SUMMARY OF THE INVENTION

The invention is directed to a system and apparatus for providing personal thermal heating/cooling as a means of physical therapy to a user onto specific areas of a body to relieve aches, pains and muscle discomfort arising from physical strains and sprains, and to counter exposure to extreme environmental conditions such as in high temperatures where cooling may prevent or mitigate a heat casualty.

An exemplary heating/cooling therapy pad system comprises a thermal therapy pad having detachable thermal inserts. The thermal inserts may be heated or cooled prior to insertion into the thermal therapy pad depending on the application. An exemplary thermal therapy pad has a plurality of insert pouches for receiving a thermal insert. A pouch gap may be configured between the pouches to provide better conformability of the thermal therapy pad around a curved surface, such as around the neck or head. A thermal insert comprises a thermal medium, such as a gel of other material which may have a high heat capacity. The type of thermal medium used may be selected based on heating or cooling. A thermal insert may be rectangular or block shaped or may be a thermal insert rod having a cylindrical shape with a diameter and length. A plurality of thermal therapy pads may be configured to detachably attach to each other via connectors, such as hook-and-loop fasteners.

In an exemplary embodiment, a thermal therapy pad has adjacent insert pouches with a pouch gap therebetween. The pouch gap may be large enough to enable curvature of the thermal therapy pad and therefore the pouch gap may be 25% or more the width of the thermal insert, 50% or more the width of the thermal insert, 75% or more the width of the thermal insert, or the width of the thermal insets or more, and any range between and including the pouch gap widths provided. A thermal insert may have a width or diameter, wherein the diameter is considered the width for the purposes of this application. A thermal insert rod may have a diameter of about 20 mm or more, about 25 mm or more, about 30 mm or more and any range between and including the diameters provided. The pouch gap may be about 10 mm or more, about 15 mm or more, about 20 mm or more about 30 mm or more and any range between and including the pouch gap distances provided.

An exemplary heating/cooling therapy pad system comprises a neck therapy pad having extensions for extending around a person's neck and an attachment on each of the extensions to detachably attach the extensions together. A neck therapy pad may further comprise a hygiene cover that is coupled to the connector and extends along an inside surface of the neck therapy pad. A hygiene cover may be used with any of the thermal therapy pads as shown as part of the heating/cooling therapy pad system and may be detachably attachable to an attachment or connector, such as hook-and-loop fastener. While the neck therapy pad is depicted with a hygiene cloth that may be used with clients in a clinical setting where the pad can be reused on another person by changing the hygiene cloth. This is a routine practice in clinics such as a physical therapy clinic where heat or cool pads are part of the treatment. Hygiene cloths are not depicted on the other pads in the figures. However, each therapy pad will come with a hygiene cloth that fits the pad so that each pad may be reused in a clinical setting.

A neck therapy pad may comprise a thermal pad portion configured between the extensions and this thermal pad portion may have a neck extension centrally located along the thermal pad portion. The neck extension may be configured to extend up a person's neck when donned and the neck extension length may be greater than the length of the thermal pad portion proximal to the extensions. The thermal pad portion may be curved, having an arc shape across a top of the thermal pad portion. An exemplary neck thermal therapy pad incorporates vertical cylinders or pouches for receiving elongated thermal inserts, such as thermal insert rods with separations that have varying lengths to ensure that the pad can effectively contoured to fit the neck and that the pad reaches above the cervical area of the neck to include the sub-occipital area of the skull. This neck extension along with the thermal insert rod and pouch gaps to allow conformability, provide great contact coverage and heat transfer with the neck. The neck therapy pad is contoured to fit the neck and that the pad reaches above the cervical area of the neck to include the sub-occipital area of the skull. This is the area where the muscles that support the head originate along the spine and then insert into the sub-occipital skull area, which is where many headaches and neck sprains and strains occur that may generate discomfort that heat or cool therapy pads may relieve.

An exemplary heating/cooling therapy pad system may comprise a chin rest configured to detachably attach to the neck thermal pad. A chin rest insert may be configured for insertion into a chin rest receiver of the neck therapy pad. The chin rest pad may support a person's chin when the chin rest is coupled with the neck therapy pad. An exemplary heating/cooling therapy pad system may comprise a head rest configured to detachably attach to the neck thermal pad. A head rest insert may be configured for insertion into a head rest receiver of the neck therapy pad. A head rest may comprise a head rest pad, which may include a thermal medium, that is U-shaped and configured to extend around a person's ear. The head rest may have shoulder extension that extend from a pivot to a shoulder support.

An exemplary heating/cooling therapy pad system comprises a spine therapy pad extending a length from a neck end to a lumbar end and configured to detachably attach to a neck therapy pad by a neck connector, such as hook-and-loop fastener. A spine therapy pad may have a plurality of insert pouches for receiving thermal inserts. The thermal insert pouches may extend along the length of the spine therapy pad or orthogonally to the length. In an exemplary embodiment, the insert pouches extend along the length of the spine therapy pad and a centrally located pouch is configured to receive a thermal insert rod that is larger in diameter than thermal inserts on either side. This centrally located thermal insert rod, or spinal thermal insert, may be larger to enable the thermal insert to conform to the concave contour of the body along the spine. In an alternative embodiment, the thermal inserts and pouches are configured orthogonally to the length and thermal insert rods may be configured in rows along the length of the spine.

An exemplary heating/cooling therapy pad system comprises a lumbar therapy pad comprising that has a plurality of insert pouches for receiving thermal inserts. Like the neck thermal therapy pad, the lumbar therapy pad has extensions for extending around a lumbar and torso of a person and attachments on each of the extensions to detachably attach the extensions together. An exemplary lumbar therapy pad comprises a connector for coupling with a lumbar attachment of the spine therapy pad.

An exemplary heating/cooling therapy pad system comprises head therapy pad that is dome shaped and configured to fit over a person's head. The head therapy pad may be elastic, wherein the outer covering is an elastic material to enable the head therapy pad to expand and contract as required to fit over a person's head. An exemplary head therapy pad has a plurality of insert pouches for receiving thermal inserts. The outer covering or material between the thermal insert pouches and thermal inserts may be an elastic material. An elastic head therapy pad may be configured to cover the forehead, extend over the ears if desired, the back of the head, and halfway down the cervical neck area as well. When used in conjunction with a neck therapy pad, the head pad may extend down to the top of the neck therapy pad to multiply the heat or cool therapy to this critical area of a user's body.

An exemplary heating/cooling therapy pad system comprises face therapy pad having a face thermal insert that is detachably attachable to the head therapy pad. A face therapy pad may have an insert pouch for receiving face thermal insert. The face thermal insert may comprise eye thermal portions configured to rest over a person's eyes when donned, especially when in a supine position.

An exemplary heating/cooling therapy pad system comprises therapy pad vest that is configured to fit over a person's shoulders and extend down along the person's back. An exemplary therapy pad vest has a plurality of insert pouches for receiving thermal inserts. An exemplary therapy pad vest has a spine receiving portion for extending over or under a spine therapy pad. The therapy pad vest may have straps that extend down from the front of the shoulder portion and around the user's arms to secure the therapy pad vest. These straps may have buckles or another length adjustment feature to enable proper fitting for a wide variety of sizes.

An exemplary heating/cooling therapy pad system comprises an armpit therapy pad having extensions for extending around the shoulder and an attachment on each of the extensions to detachably attach the extensions together. Armpit therapy pads may be used to reduce a person's body temperature, such as when they suffer from heat exhaustion. Athletic trainers and healthcare providers may use the armpit therapy pad for cool therapy as an essential treatment of a heat casualty, which is best treated by applying cooling to critical areas of the body where vasoconstriction and cooling of the blood circulation and core body temperature is facilitated. Cooling to treat a heat casualty is most effective when applied to the head, neck, forehead/eyes, armpits, wrists, and groin areas over other body areas. The present invention provides a set of cooling therapy pads that can effectively treat minor overheating and life-threatening heatstroke by applying cooling to the head, neck, forehead/eyes, armpits, and the groin area can be cooled by the spine or lumbar pad as well.

The present invention relates to a system of thermal pads that cover the head, eyes, neck, spine (thoracic region), lower spine (Lumbar region), shoulders, and arm pits. The system of pads interconnect with each other to tailor thermal therapy for the user. There are numerous types of thermal heating/cooling pads that can be applied to a user's body but all existing designs lack the capability to combine and interconnect heating and cooling thermal therapy treatments concurrently to the user and over a number of body areas to create a more effective integrated therapy system than prior art and current products in the market.

The unique and novel features of the present invention provide the user with an efficient and readily adaptable integrated system to fulfill a number of specific novel capabilities.

All people experience minor aches, pains, stiffness, and strains. These minor injuries are best treated initially and periodically with thermal therapy of either heat or cool applications. In general, heat is used for muscle pain and stiffness because it increases the blood circulation to the affected areas, which brings some level of relief and it promotes healing and recovery. Cool therapy is typically applied for acute injuries or pain, swelling, and inflammation and it too aids in healing.

Heat therapy is most effective for a minimum of 15-20 minutes, although longer times (30-120 minutes) are often effective as well. Cool therapy, especially if near freezing ice applications are used, are best used for 15-20 minutes or less depending on the temperature and how much it causes discomfort to the skin or even damage. Cool therapy also increases blood circulation but is best for reducing inflammation, swelling and pain. In fact, alternating between heat and cool therapies for acute injuries has been shown to be more effective than using only heat or cool therapy alone.

The system described here may use commercial off-the-shelf (COTS) organic filler materials for the heat tube such as buckwheat or flax seed, or farro and COTS chemical gel inserts may be used for cooling therapy. Some of the heat pads in the market are advertised as being effective as a cool therapy pad. However, product testing demonstrates that pads using vegetable matter may be cooled, but the cooling effect is not perceived as sufficiently cool by users and the cooling effect quickly dissipates. The most effective cooling pads are those filled with a fluid or gel chemical insert that can be cooled in a refrigerator, freezer, or ice- and water-filled cooler. Such pads can be cool for maximum effect without being too uncomfortable to the skin, and the pads provide cooling for a relatively long period of time.

Given that the material inside a pad does not work equally well for heat or cool therapy, it is more effective to manufacture thermal therapy pads that are optimized to provide either heating or cooling alone. However, for some therapy pads that may have simple repeatable designs, creating pouches inside the pads where heat or cool therapy inserts may be interchanged is an effective and economical solution. An exemplary thermal therapy system may have pads that are for heat only, cool only, or the thermal inserts may be similar in size and interchangeable to provide either heat or cool therapy as part of the system. Hereafter, for this invention, heat therapy is provided by an array of single or dual tubes and cool therapy is provided by an array of gel inserts.

An exemplary thermal therapy system may have seven heat/cool thermal pads that are designed to provide therapy to a primary body region. The thermal pads such as the neck pad has a unique design in that each pad has industry standard natural vegetable materials such as buckwheat, flax seed or farro for heat therapy or chemical beads and gel/fluid in a bag that provides cooling therapy to the user. The integrated system described here may include adjustable, one-size-fits-all pads for the head, forehead and eyes, neck, spine (thoracic region), shoulders and the sides of the back, the lumbar region of the back, and within the arm pits.

Each pad may be composed of outside cloth enclosing the thermal materials. The heating materials may be filled inside an internal cloth cylinder or tubular shape and then sewn closed. The heat tubes may be sewn together with other filled tubes and with the outer cloth material to form a tailored shape to fit the user's body region. The tubes may create some separation between each other to reduce weight and volume and allow some air to circulate between the tubes, which improves heat transfer.

The pads may have two sides; one inside that is placed against the user's body, and an outside away from the body where there can be one or more layers of heat retaining thermal insulation barriers such as silk, meta-aramid or para-aramid material as one layer and a second outer layer of wool.

The heat/cool chemical or organic material is a COTS item; the patent is for the unique design of the system comprising the separate pad components or types that are integrated and interconnected together to provide temperature therapy to the 1) neck, 2) head, 3) forehead and eye sockets, 4) spine (central thoracic region), 5) shoulders (shoulder blades and over each shoulder to the clavicle region), 6) lumbar region (below shoulder and spine pads), and 7) underarm pads for each armpit region. In addition, each pad has a unique internal design of tubular and flat thermal elements that are not found in the prior art or in marketed products.

The thermal heat tubes may be aligned within the thermal pads with some separation that reduces the weight of the pad and the volume of the heat-retaining material, which may reduce the heating time in a microwave oven. The combination of the dimensions of the heating tubes or cooling inserts and the pad shape may improve the fit of the given pad to the intended region of a user's body, which also may provide more effective thermal therapy than if the pad were filled by the thermal material inside in a single amorphous shape.

Each thermal pad may be individually secured to the body by adjustable straps/belts without being interconnected to another pad. However, each of the pads may be readily secured and interconnected with other adjacent body region pads by hook and loop fasteners and belts/straps to provide more effective thermal therapy over a wider area of a user's body. In most instances, it may be that the when a user requires thermal therapy, the therapy is more effective when it is applied to more regions of the body based on the user's preference. For instance, the spine neck pad may have a fastener in the top to secure it to the neck pad and another fastener at the bottom to secure it to the lumbar pad.

Aside from the hook and loop fasteners securing the thermal pads together, there may be snap-on fasteners with straps (aka belts) that may be adjusted to tighten the pads for more direct application to the user's body for greater effect as well. There may be two straps for the spine pad, two straps for the shoulder pad, and two straps for the lumbar pad. The adjustable shoulder pad straps may crisscross over the front chest of the user to provide greater security, tightness, and comfort.

The combination of hook and loop and strap fasteners allows for a lot of flexibility in which pads may be used for therapy and for how tight the user prefers a pad to feel against their body. Both sides of the hook and loop fasteners may be located on the outside of the pads so that they do not touch the user's skin.

The pads may have covers made of soft cloth that may be placed over the pad to cover the surface against a user's skin and provide a hygienic barrier between the user and pad. This allows the cover to be replaced after each use and a clean cover to be attached for another user in places such as a physical therapy facility. In other words, the inside segments of a pad where the heat or cool is emitted may not touch the user so that these surfaces remain cleaner longer and safely allow for other users such as in a clinical setting.

The neck pad may have accessories that can be tightly fitted into slots on the outside of the pad. The chin support accessory may have a forked piece that inserts into slots in the neck pad to hold it in place and then a padded and curved chin rest piece may be used to comfortably rest the chin upon when desired by the user. In addition, there may be side accessory supports that may also be tightly fitted with forked pieces into slots on the outsides of the neck pad. These supports have a padded and curved piece to comfortably support the head on each side. The head support may be U-shaped to fit on each side around the user's ears. Another hinged piece may fold out from below the ear to allow another curved part of the side head support to rest upon the users top shoulder. These accessories may help stabilize the head so that the user can comfortably rest or sleep in an upright head position when desired or required when sitting such as in an airplane seat or sofa chair.

The key to the neck pad and how it may be more effective than other products in the market is in the shape of the heat chemical tubes or cylinders and the way the tubes inside each pad are sewn. For instance, the pads for the neck may have a vertical tubular organization with a separation between each tube filled with heat emitting material when the pad is laid flat. The unique design of the separated vertical tubular elements in the neck pad may provide effective and sustained thermal therapy. The concept is that as the neck pad is wrapped around the neck, each separated vertical element may come together to create a continuous thermal surface against the skin. This design may also produce a lighter product and it may take less time to heat the pads relative to the more bulky and voluminous thermal therapy pad products in the market.

The system may provide for the user to select individual heating and cooling body locations based on the specific area of need. For example, the lumber pad may be used by itself by its straps or it can be integrated with the spine, thoracic, and shoulder pads where hook and loop fasteners connect the pads together. In addition, the pads may be used on other body parts such as the stomach, abdomen, arms or legs because the fasteners and straps allow for such flexibility in use.

The inventive concept may incorporate the use of COTS thermal transfer material that are placed in novel tubes in a modular configuration that are placed vertically inside the heat pads such as the neck pad. For the spine pad, the heat tube in the center may be larger in diameter than the adjacent tubes on either side so that a contouring of tubes results in the central spinal region receiving more concentrated thermal therapy once the fasteners are adjusted for maximum effect. The fastener straps may be attached on the outside of the pliable spine pad so that when the straps are tightened the larger central tube presses in more to effectively fit the contour of the user's body. The side pads may also contour to the adjacent region of the back to provide a well distributed thermal therapy to the spine.

Since the construction of the heat/cool pads may incorporate layers of thermal retaining barriers on the outside of the thermal material to reduce heat less that may also enhance thermal transfer to the user's body, which means that the pads remain relatively warmer or cooler for a longer period of time.

Further, the instant invention may provide the means to tailor the system to meet specific heating or cooling therapy needs of the user. While the pads are identified as being intended for a specific area of the body, the pads are also easily adapted for use on other body areas such as arms and legs. In effect, the system has applications beyond those described here and what is described here is not limiting in the application of the invention to other uses as a body therapy system. The heat/cool therapy system is intended for child and adult humans within normal ranges of height and weight. However, the system may also be applied for select animal use as long as such use is recommended by a veterinarian, the size of the animal falls within the adjustment range of any of the pads, and the user ensures the pads are not too hot or cold before being applied to the animal.

The novel system invention may provide the means to treat a variety of user medical treatment needs including, but not limited to, conditions such as spinal stenosis, sprains, strains, muscle tissue damage, and migraine or other headaches. In short, any condition where thermal therapy may alleviate or mitigate the pain or discomfort, this invention may be efficient and effective as a treatment therapy for the body areas directly covered by the system of pads or to other body areas where the pads may be tailored for use.

It should be noted that the individual components of the novel inventive concept may be stain resistant and readily washable using conventional washing machines and dryers. The thermal materials and cloth used to produce the pads may also be infused with aromatic chemicals that enhance the smell of the pads when they are used for heat therapy.

The manifold features of the heating/cooling pad therapy system comprise an integrated system where the whole is greater than the sum of its parts. The combination of pads and their ability to be interconnected and interchanged between heating and cooling therapy is unique. The set of pads comprising the system cover the critical body regions recognized for the benefits that heat or cool therapy may provide. In addition, the system of pads also provides the capability and flexibility to effectively apply tailored therapy to a user's extremities and other core body areas such as the groin, abdomen, stomach, torso, and buttocks when needed. Hence, the invention as a set of pads is best viewed as an integrated and comprehensive system onto itself.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
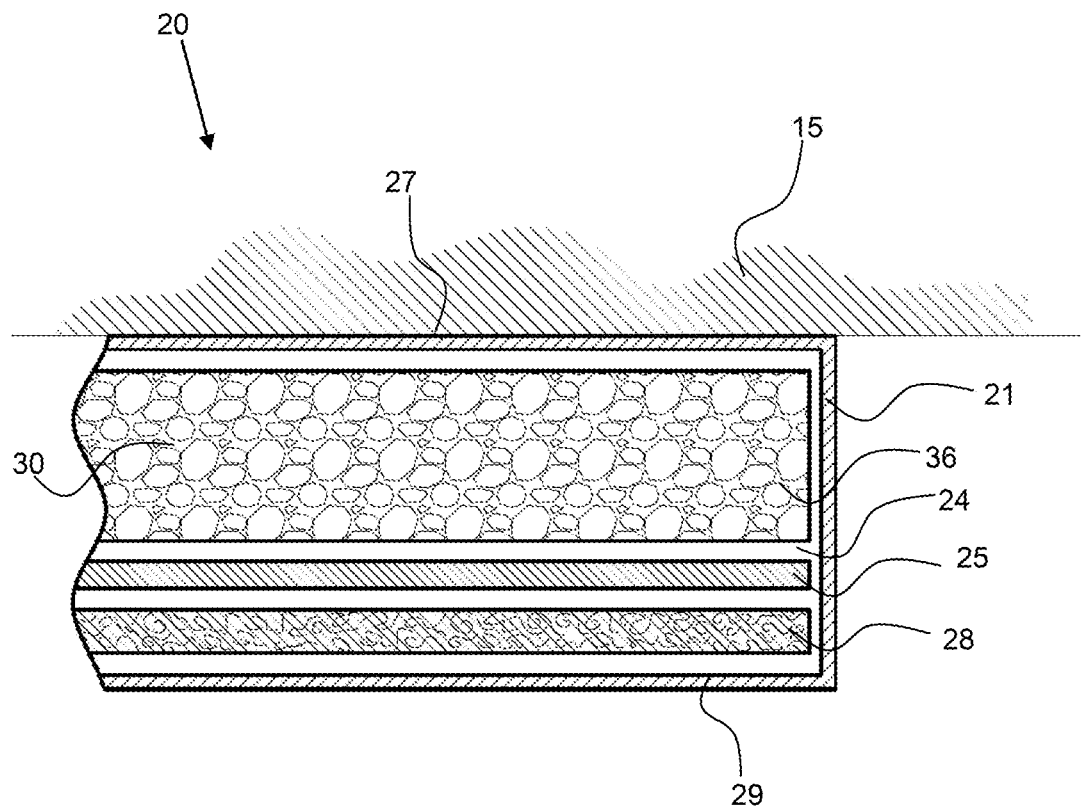
FIG. 1 shows a cross section view of the internal components of an exemplary thermal therapy pad.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components.

Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary thermal therapy pad 20 comprises a thermal medium 36 in a thermal insert 30 that is configured in an insert pouch 24 of the thermal therapy pad. The thermal medium may be configured for heating or cooling. A thermal therapy pad has an outer covering 21 and may include a thermal insulator 28 prevent heat loss from the outer surface 29. The thermal insert and insert pouch are configured proximal to the inner surface 27 of the thermal therapy pad, for placement against the body 15. A thermal retainer layer 25, such as a layer comprising meta-aramid, para-aramid, foam, such as closed cell foam, or silk may form the insert pouch 24 within the thermal therapy pad 20.

Figure 2:
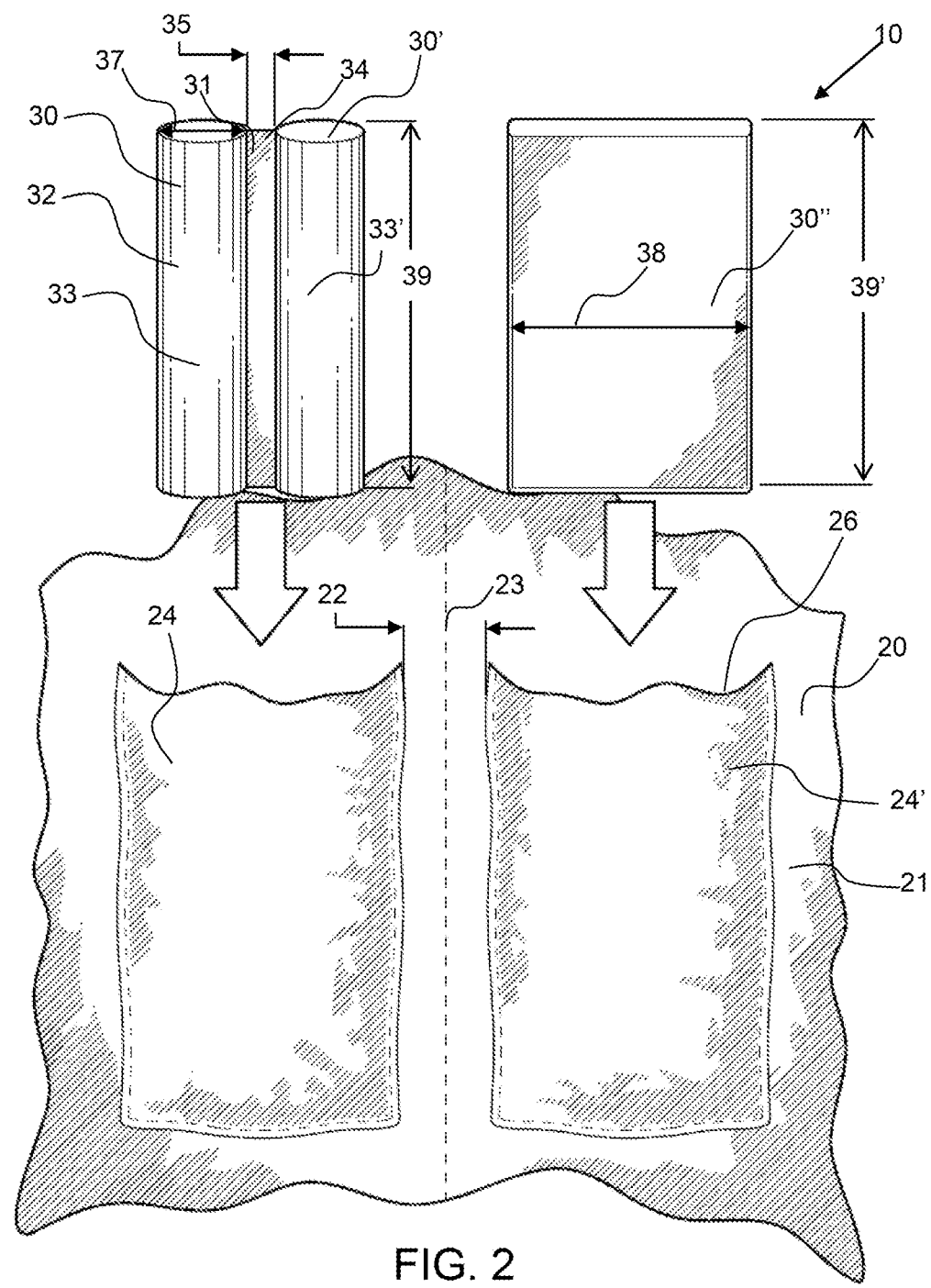
FIG. 2 shows a perspective view of the dual thermal insert and a single rectangular thermal insert and how each fit into an insert pouch of an exemplary thermal therapy pad.

As shown in FIG. 2 shows an exemplary thermal therapy pad 20 comprises a pair of thermal insert pouches 24, 24'. A dual thermal insert 32 is being inserted into the first insert pouch 24 and a single rectangular thermal insert 30" is being inserted into the second insert pouch 24'. A pouch gap 23, having a pouch gap distance 22, is configured between the first and second insert pouches and includes the outer covering 21 of the thermal therapy pad. Each of the insert pouches have a pouch opening 26 for insertion of the thermal inserts. The rectangular thermal insert 30" has a width 38 and a height 39'. The dual thermal insert 32 has two thermal insert rods 33, each having a diameter 37 and height 39, wherein the thermal insert may be an elongated thermal insert having a length that three times or more, four times or more, five times or more, or even 10 times or more the width of the thermal insert. The dual thermal insert is configured with a thermal insert gap 34 having a thermal insert gap distance 35 between the two thermal insert rods 33, 33', for better conformability. Each of the two thermal insert rods have a discrete thermal medium separated from the other. An insert connector 31 extends between the two thermal insert rods.

Figure 3:
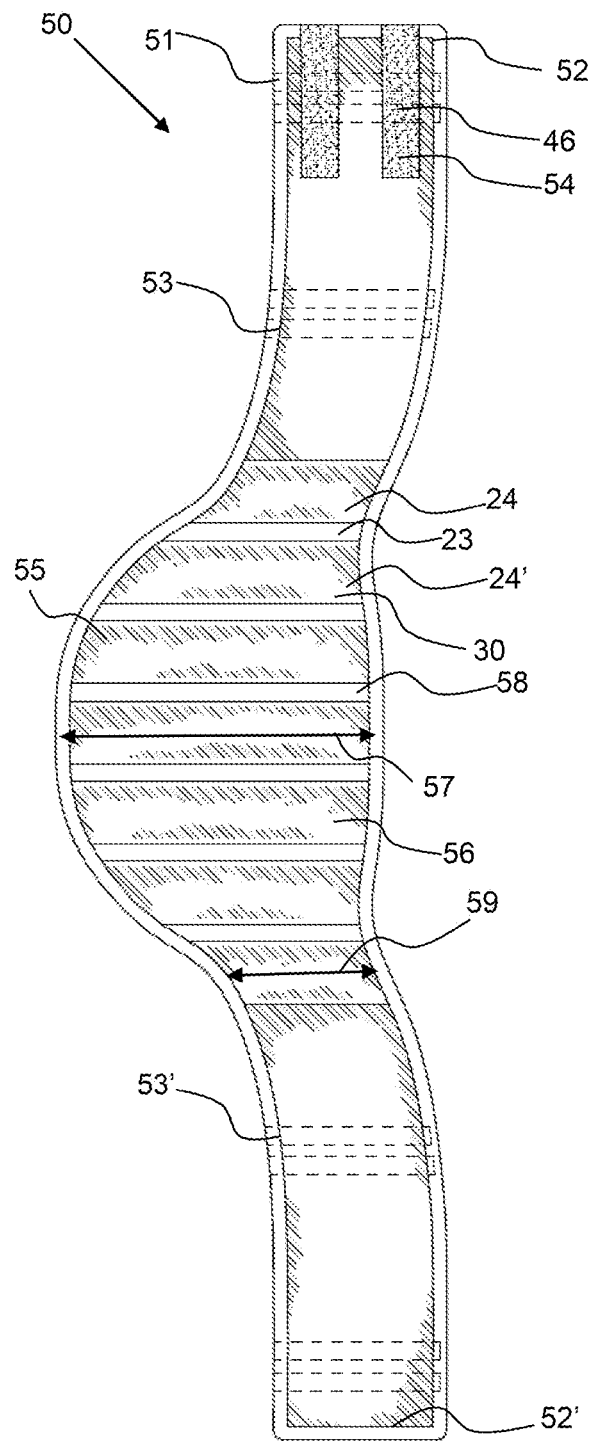
FIG. 3 shows a perspective view of an exemplary heating/cooling therapy pad system and in particular the inside of an exemplary neck therapy pad having a plurality of thermal insert pouches for receiving thermal inserts and a pouch gap therebetween.
Figure 4:
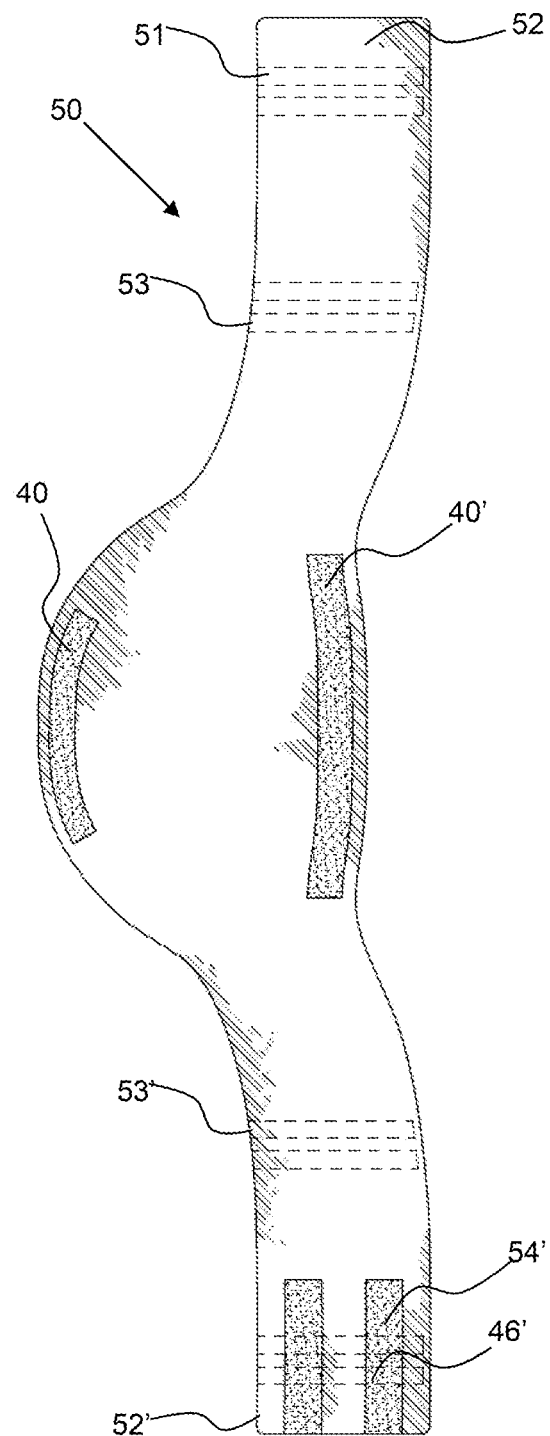
FIG. 4. shows a perspective view of the outside of the neck therapy pad shown in FIG. 3.
Figure 8:
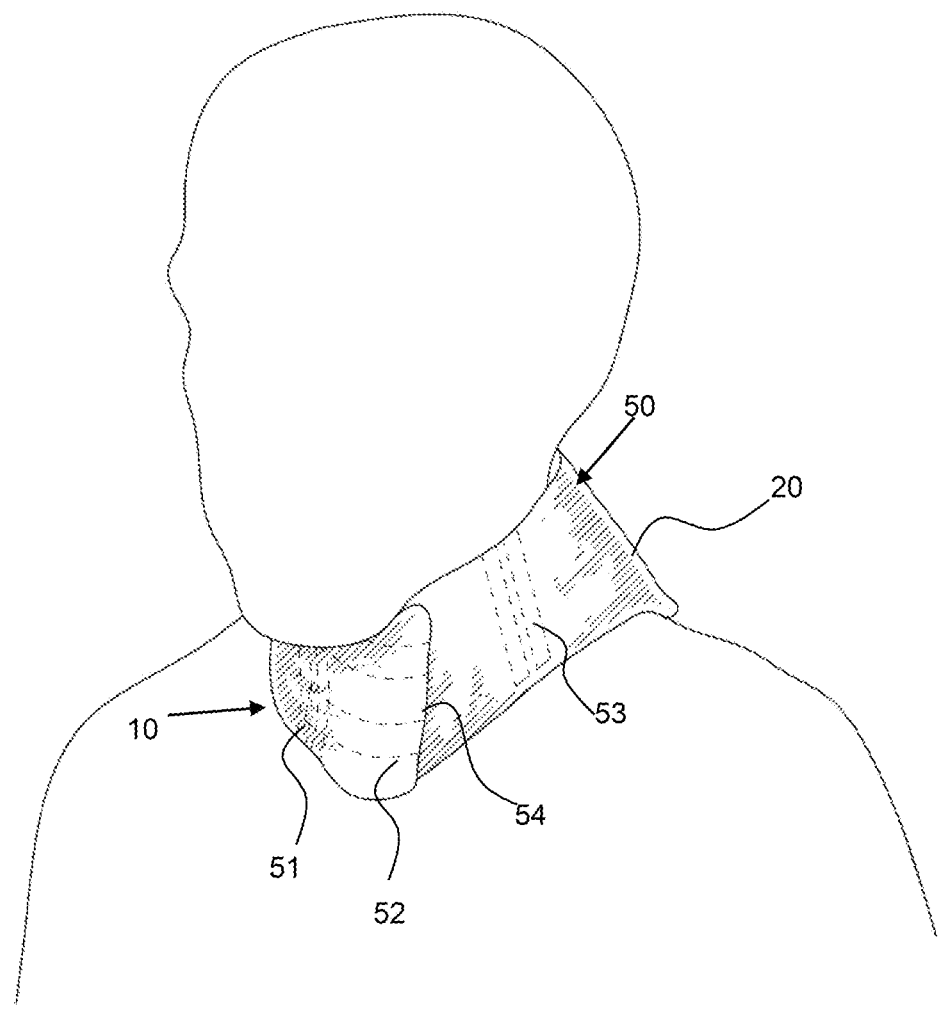
FIG. 8 shows a perspective view of an exemplary neck therapy pad fastened around a user's neck.
Figure 9:
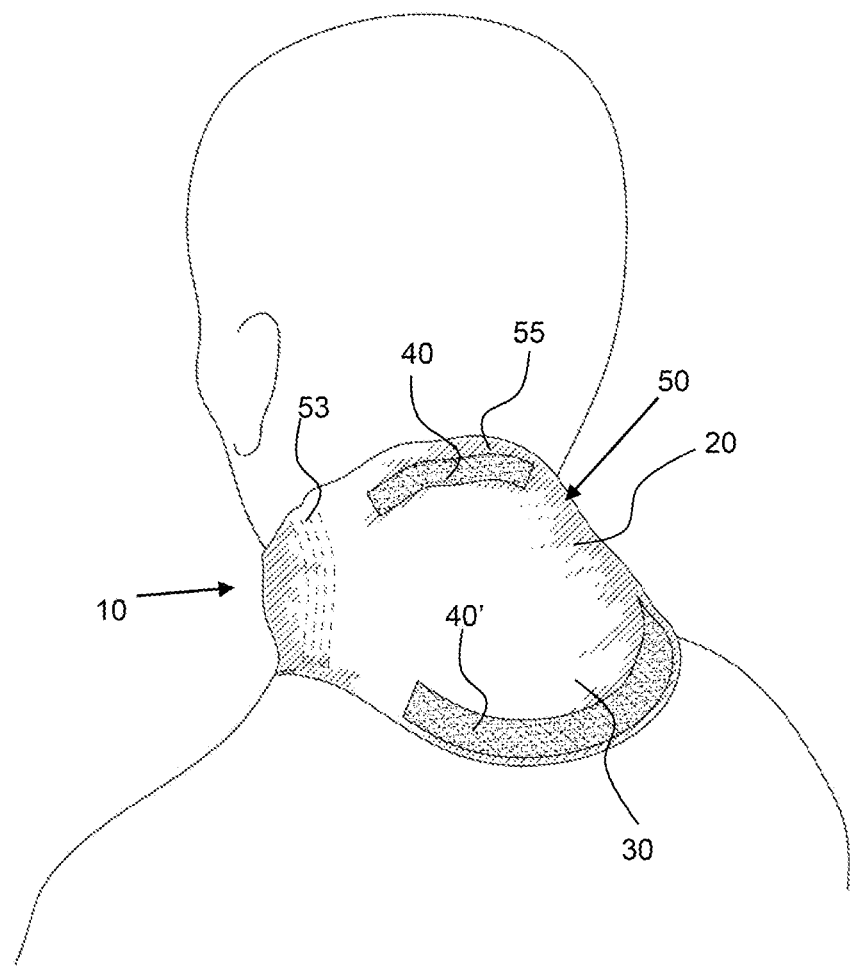
FIG. 9 shows a perspective view of an exemplary neck therapy pad fastened around a user's neck.

Referring now to FIGS. 3 to 9, an exemplary heating/cooling therapy pad system 10 comprise a neck therapy pad 50 has a plurality of thermal insert pouches 24, 24' for receiving thermal inserts 30 therein. A pouch gap 23 is configured between the thermal insert pouches to provide better conformability of the thermal inserts to a curved neck region. The neck therapy pad has extensions 52, 52' that extend from the thermal pad region that are configured with attachments 54, 54' for detachably attaching the extension together around a person's neck, as shown in FIGS. 8 and 9. The attachment may be hook-and-loop fasteners 46, 46' as shown in FIGS. 3 and 4. An exemplary neck therapy pad 50 may include a chin rest receiver 51, such as a slot or receiving channel for receiving a chin rest insert and may have a pair of head rest receivers, 53, 53' such as a slot or receiving channel, for receiving a head rest insert therein. An exemplary neck therapy pad may have a unique shape, wherein the thermal pad portion is non-uniform in length, or height when donned around the neck. The center of the thermal pad portion 56 may be longer and have a neck extension 55 having a neck extension length 57 that is greater than a length 59 of the thermal pad portion proximal to the extensions 52, as shown in FIG. 3, to enable the thermal pad portion 56 to extend up higher on the neck and the back of the skull, as shown in FIG. 9. The neck extension, or the thermal inserts of the neck extension may be 20% longer or more, 30% longer or more, 50% longer or more the length of the thermal insert proximal to the extensions, or any range between and including the percentages provided. The thermal pad portion 56 may have a curved outer edge, that may extend in an arc, as shown in FIG. 3 to provide a comfortable fit up around the back of the neck as shown in FIG. 9. As shown in FIG. 9, the top of the thermal pad portion 56 extends up along the person's neck. An exemplary neck therapy pad 50 may have a connector 40' for coupling with another therapy pad, such as a spine therapy pad. The connectors may comprise hook-and-loop fasteners.

Figure 5:
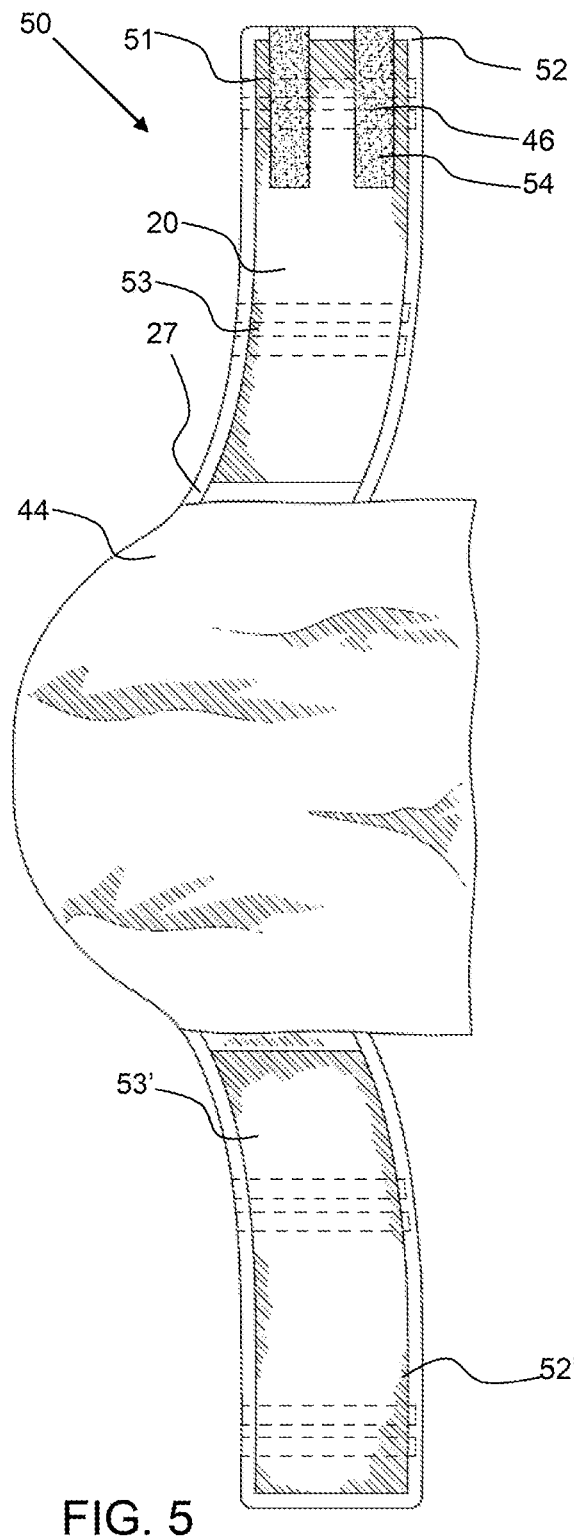
FIG. 5. shows a perspective view of the inside of the neck therapy pad shown in FIG. 3, with a cloth hygiene cover coupled thereto by the connectors.
Figure 6:
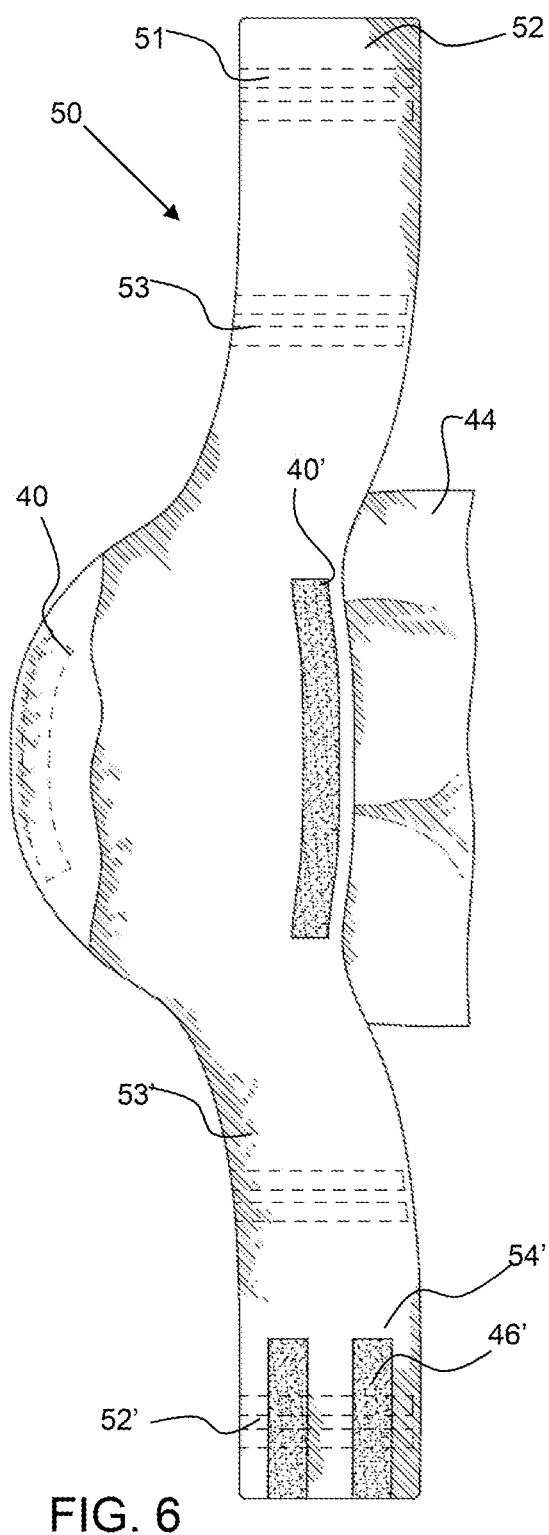
FIG. 6 shows a perspective view of the outside of the neck therapy pad shown in FIG. 4, with a cloth hygiene cover attached to the top connector and overlaying the inside of the neck therapy pad.
Figure 7:
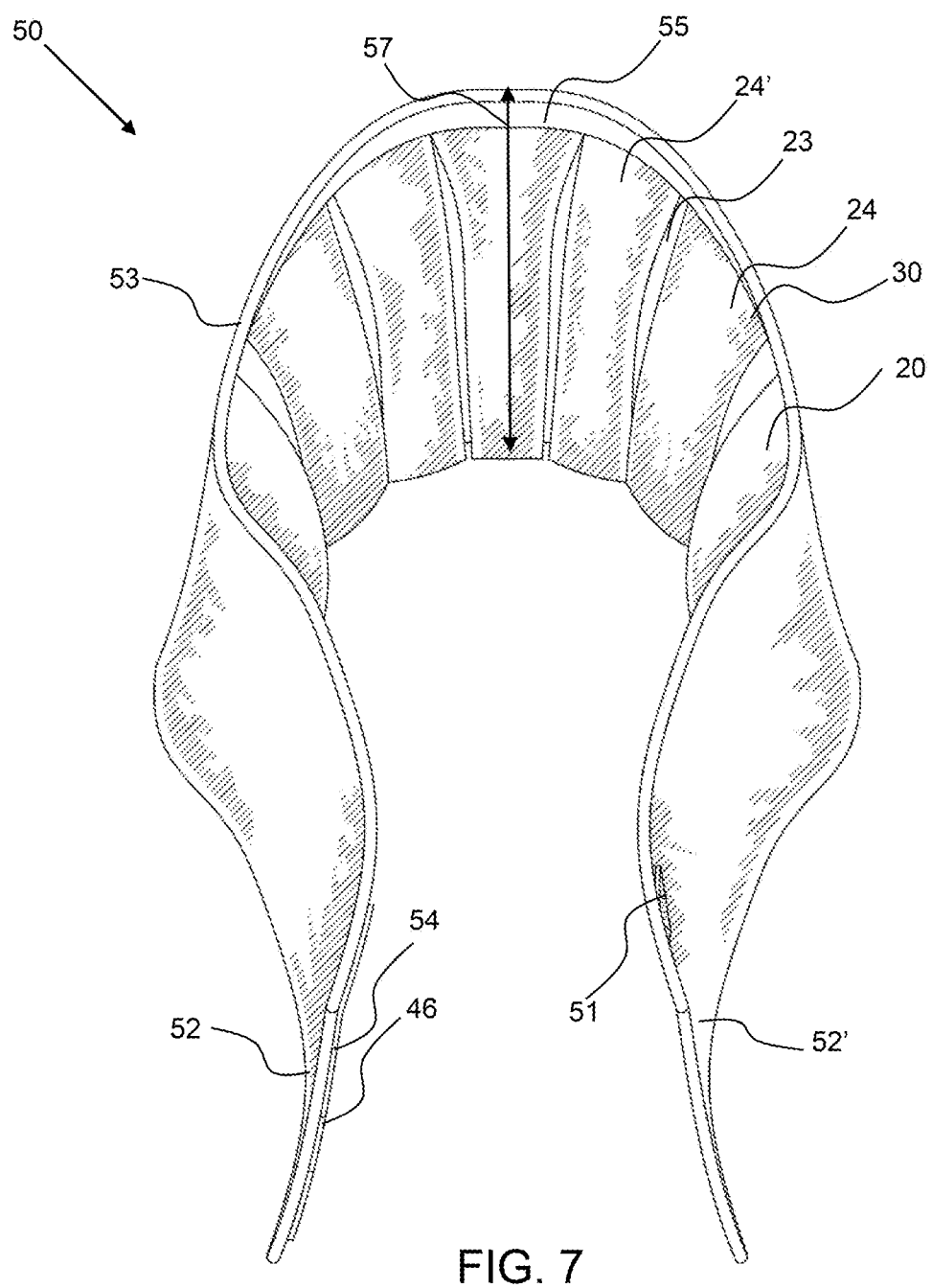
FIG. 7 shows a perspective view of the inside of a curved neck therapy pad with cylindrical thermal inserts configured in the thermal insert pouches.

As shown in FIGS. 5 and 6, a hygiene cover 44 may be detachably attached to the exemplary neck therapy pad 50 by a connector 40. The hygiene cover 44 may be used to prevent direct body contact with the inner surface 27 of the thermal therapy pad 20.

Figures 10, 11:
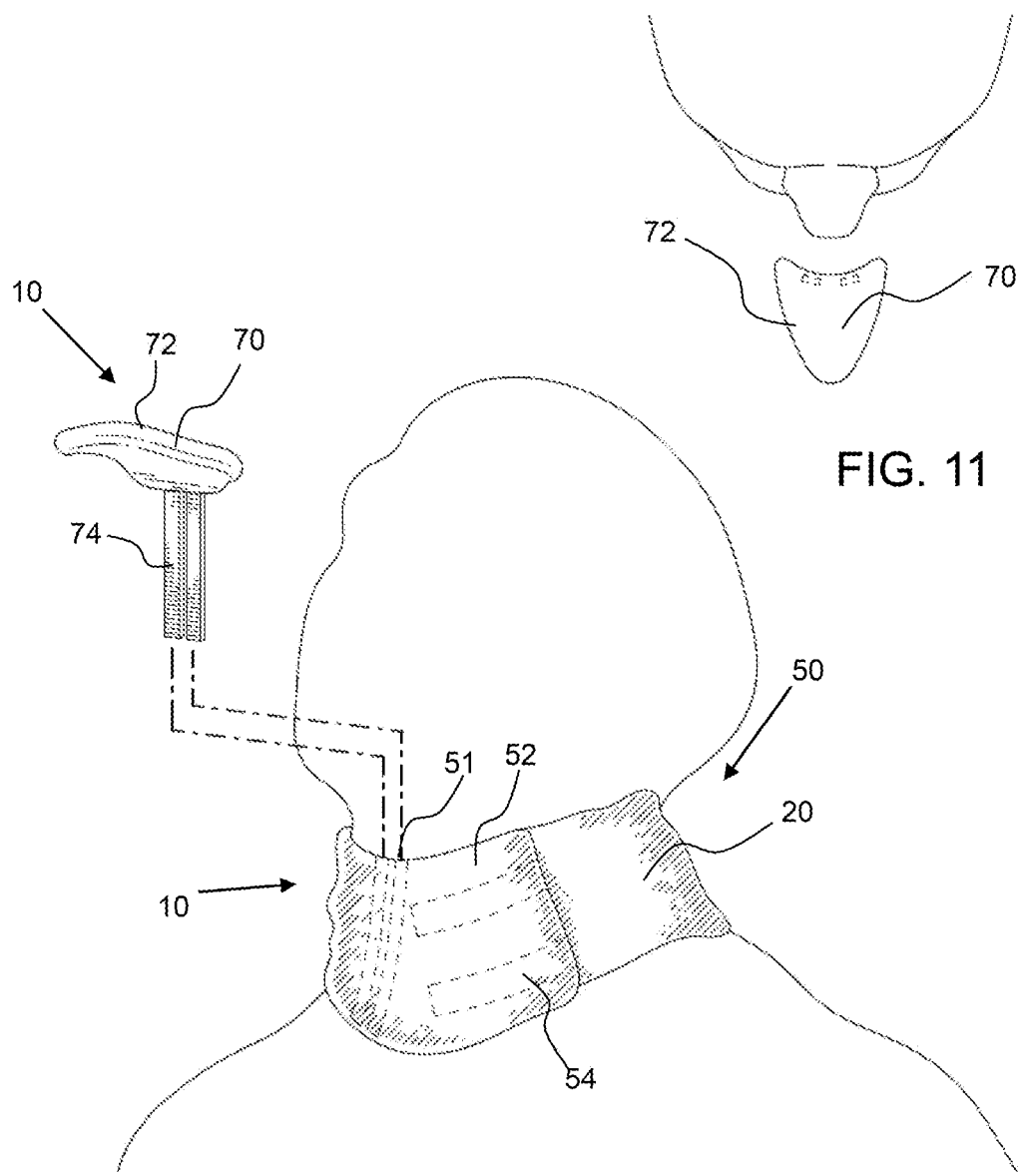
FIG. 10 shows a perspective view of an exemplary heating/cooling therapy pad system and in particular an exemplary neck therapy pad with a chin rest configured for insertion into the chin rest insert of the neck therapy pad.
FIG. 11 shows top view of an exemplary chin rest.
Figure 12:
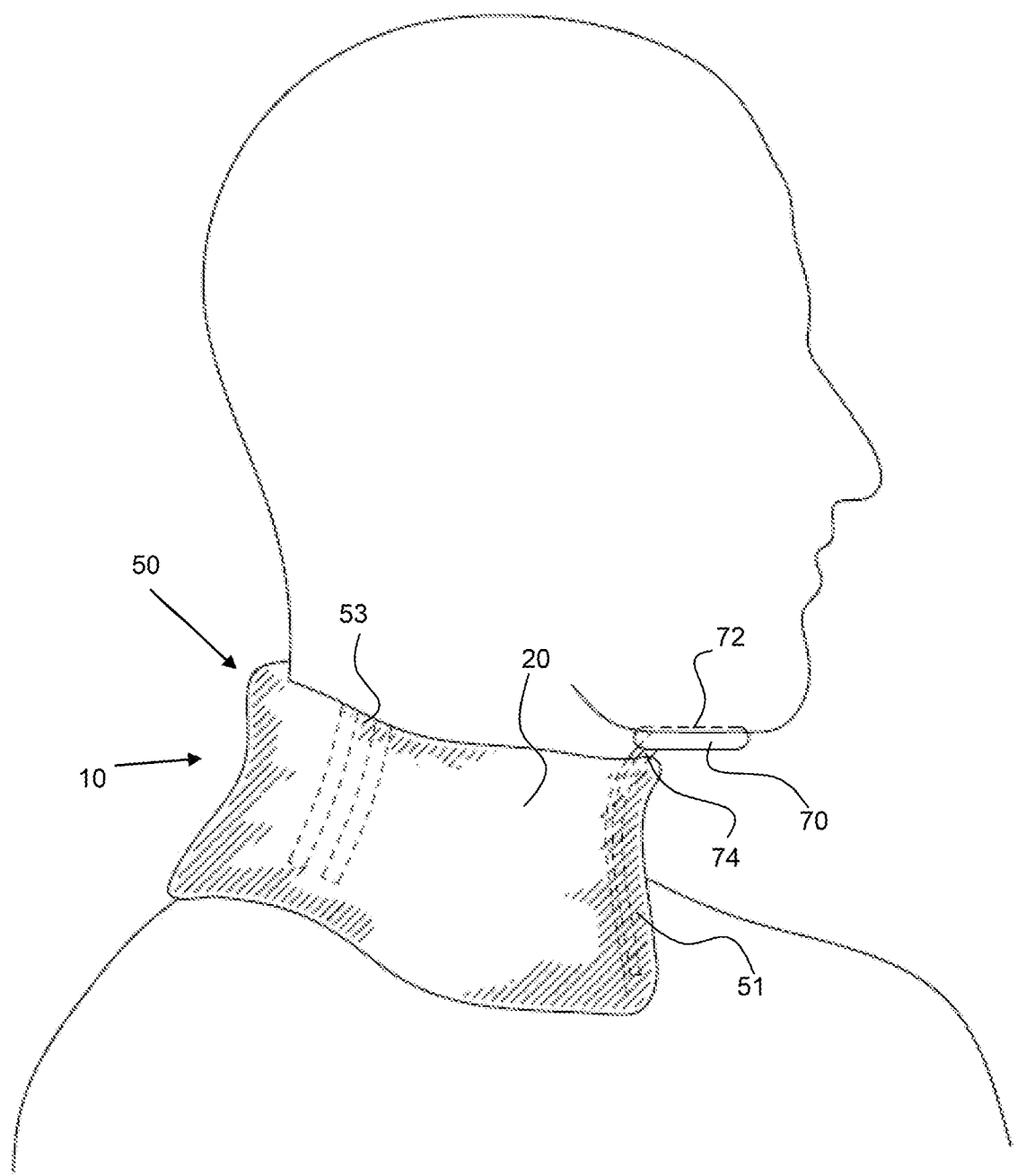
FIG. 12 shows a perspective view of an exemplary neck therapy pad with a chin rest configured into the chin rest insert of the neck therapy pad.

Referring now to FIGS. 10 and 12, an exemplary heating/cooling therapy pad system 10 comprise an exemplary neck therapy pad 50 that is configured with a chin rest 70 having a chin rest insert 74 configured in the chin rest receiver 51 of the neck therapy pad. The chin rest has a chin rest pad 72 coupled with the chin rest insert and as shown in FIG. 12, the chin rest pad provides a comfortable support for the person's chin.

Figure 13:
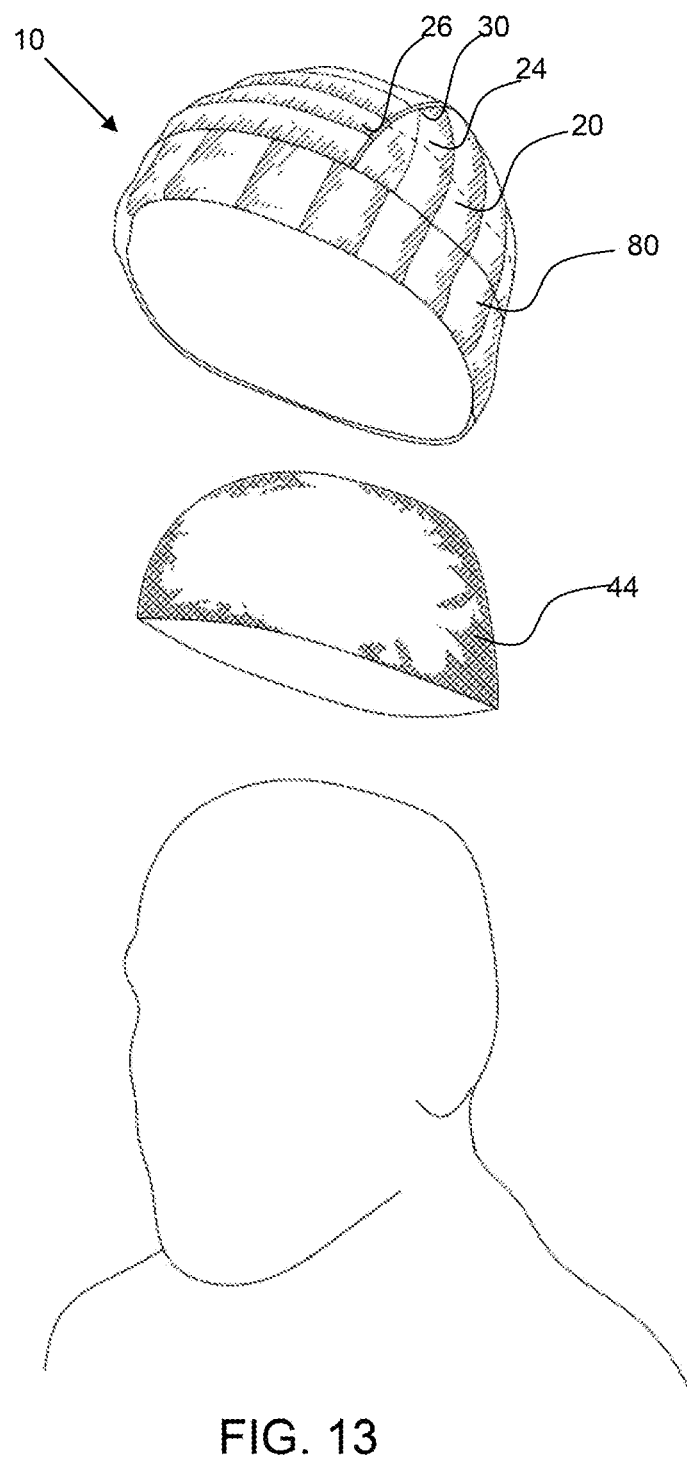
FIG. 13. shows a perspective view of an exemplary head therapy pad with an elastic hygiene cover for placement over a user's head.
Figure 14:
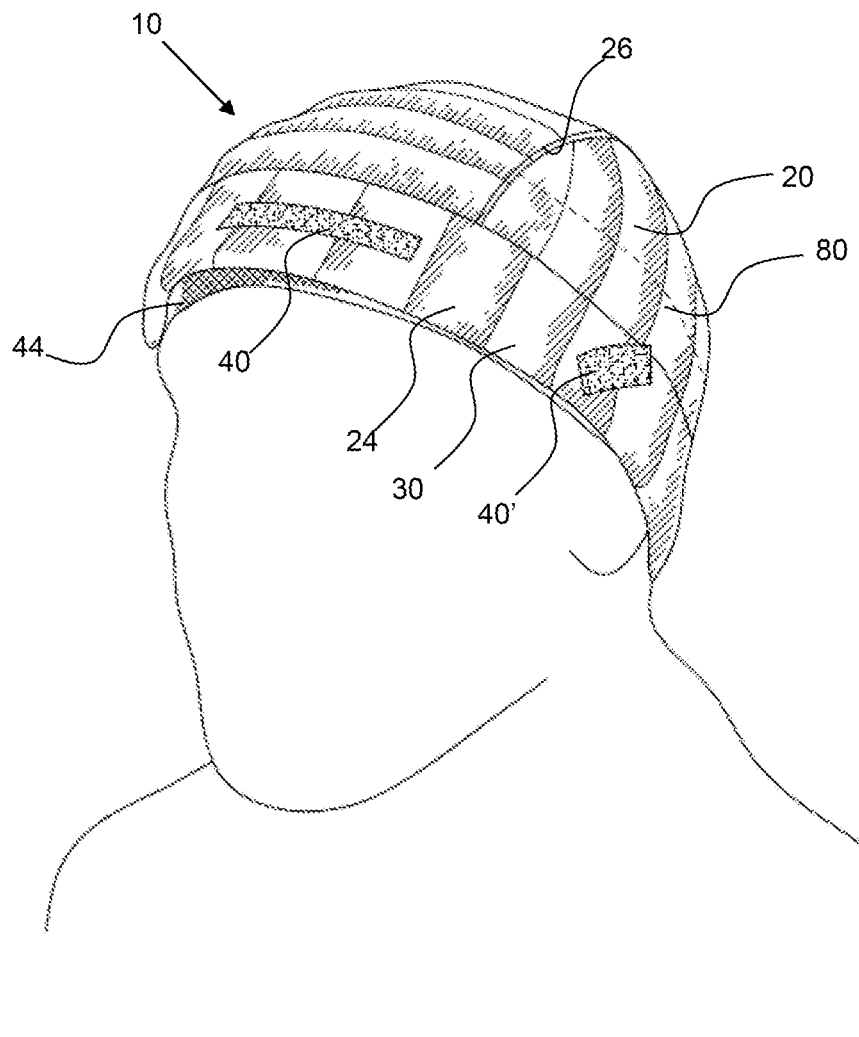
FIG. 14 shows a perspective view of an exemplary head therapy pad placed on a user's head with the hygiene cover between the pad and the person's head.
Figure 15:
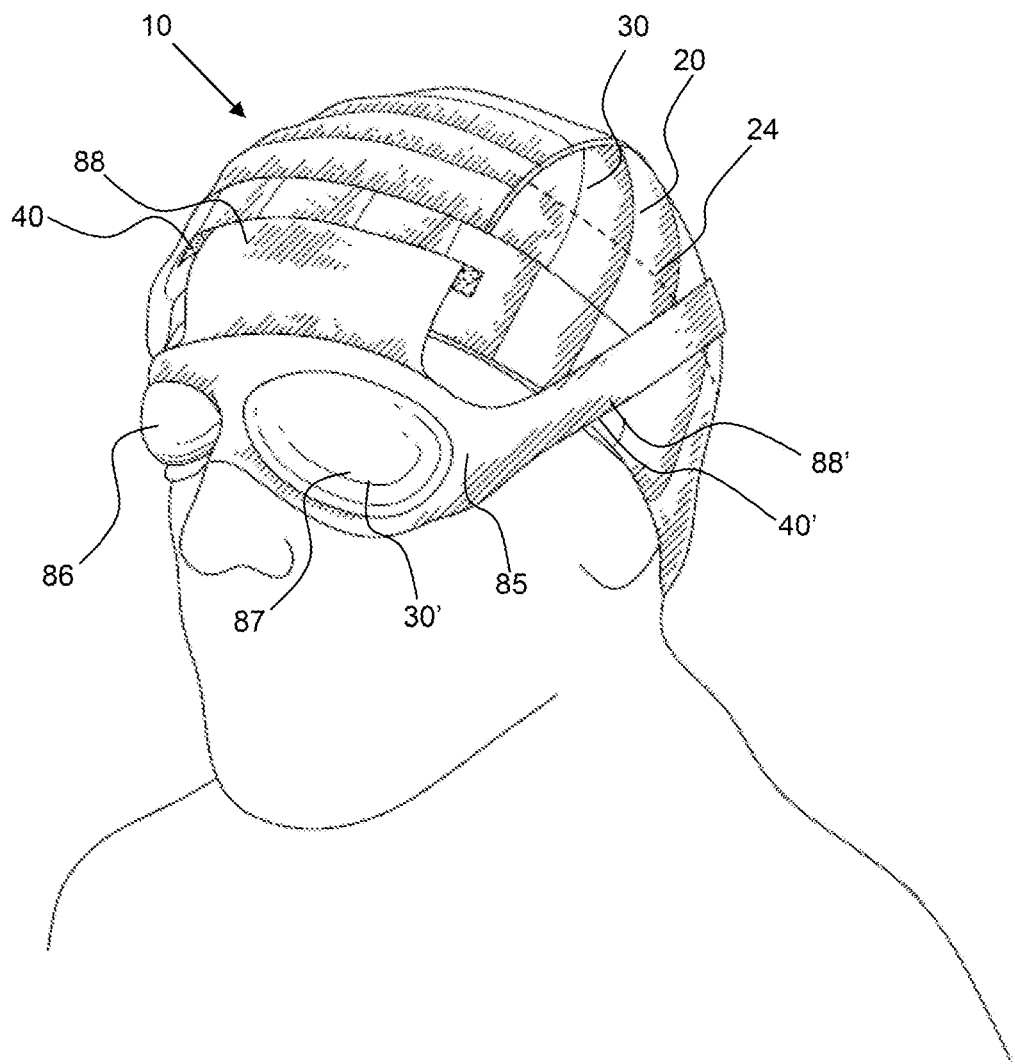
FIG. 15 shows a perspective view of an exemplary heating/cooling therapy pad system and in particular the face therapy pad covering the eyes and detachably attached to the head therapy pad by connectors.

Referring now to FIGS. 13 to 16, an exemplary heating/cooling therapy pad system 10 comprises an exemplary head therapy pad 80 that may be configured with a plurality of thermal pads and these thermal pads may be thermal inserts 30 configured to fit within an insert pouch 24. In an exemplary embodiment, some of the thermal pads are fixed and secured to the head therapy pad and some are thermal inserts. The head therapy pad 80 may be elastic, wherein the outer covering comprises an elastic fabric to enable the head therapy pad to expand and/or contract around a person's head. The head therapy pad may be a one-size fits all pad. As shown in FIG. 13, a hygiene cover 44 may be configured between the head therapy pad 80 and the person's head. As shown in FIG. 14, the head therapy pad 80 is donned over a person's head and has a plurality of connectors 40, 40' for detachably attaching a face therapy pad 85, as shown in FIG. 15.

Figure 16:
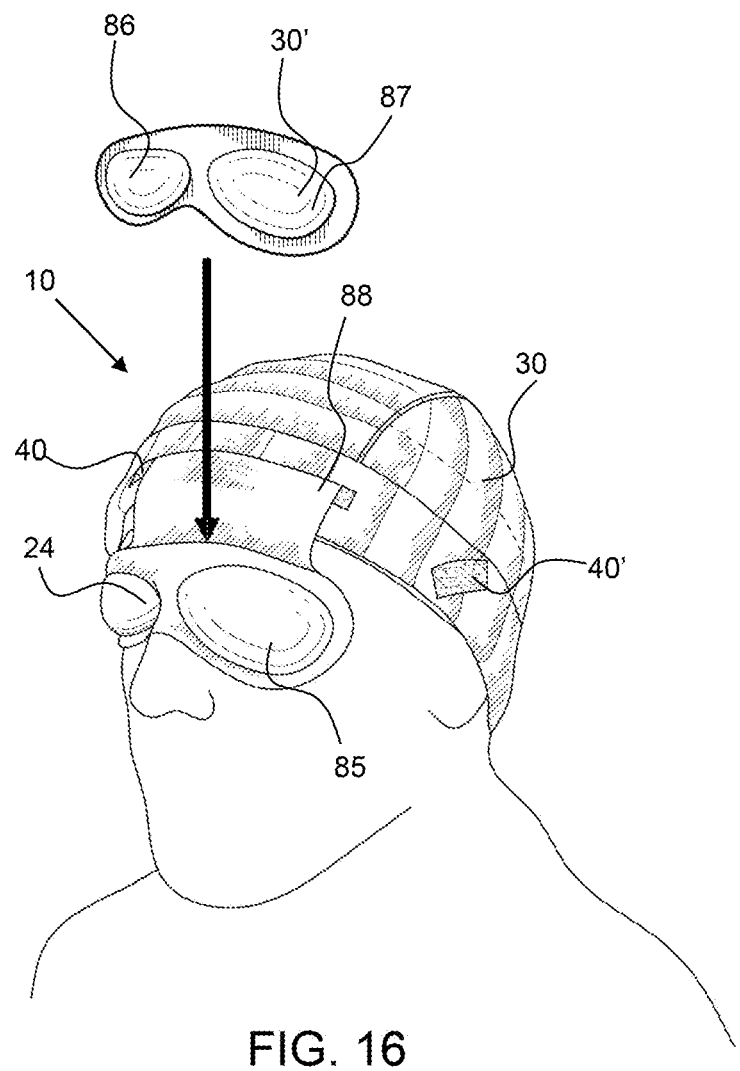
FIG. 16 shows a perspective view of the face therapy pad and the detachably attachable face thermal insert configured for insertion into a thermal insert pouch of the face therapy pad; note that the face thermal insert comprises two eye thermal inserts.
Figure 17:
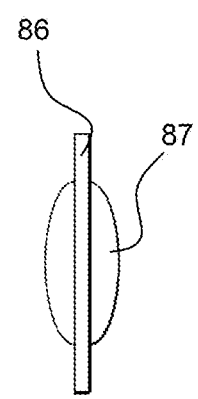
FIG. 17 shows a side view of face thermal insert having two separated thermal portions.

As shown in FIG. 15, an exemplary face therapy pad 85 is detachably attached to the head therapy pad 80 by attachment extensions 88, 88' that extend to the connectors 40, 40' on the head therapy pad. It is to be understood that the face therapy pad may have a complimentary extension to 88' on the opposing side of the person's head. The face therapy pad has a face thermal insert 86 having an eye thermal portion 87 for each eye. As shown in FIG. 16, the face thermal insert 86 is detached from the face therapy pad 85. As shown in FIG. 17, the eye thermal portion may bulge from the face thermal insert to enable the eye thermal portion to conform to the eye depression of a person's face.

Figure 18:
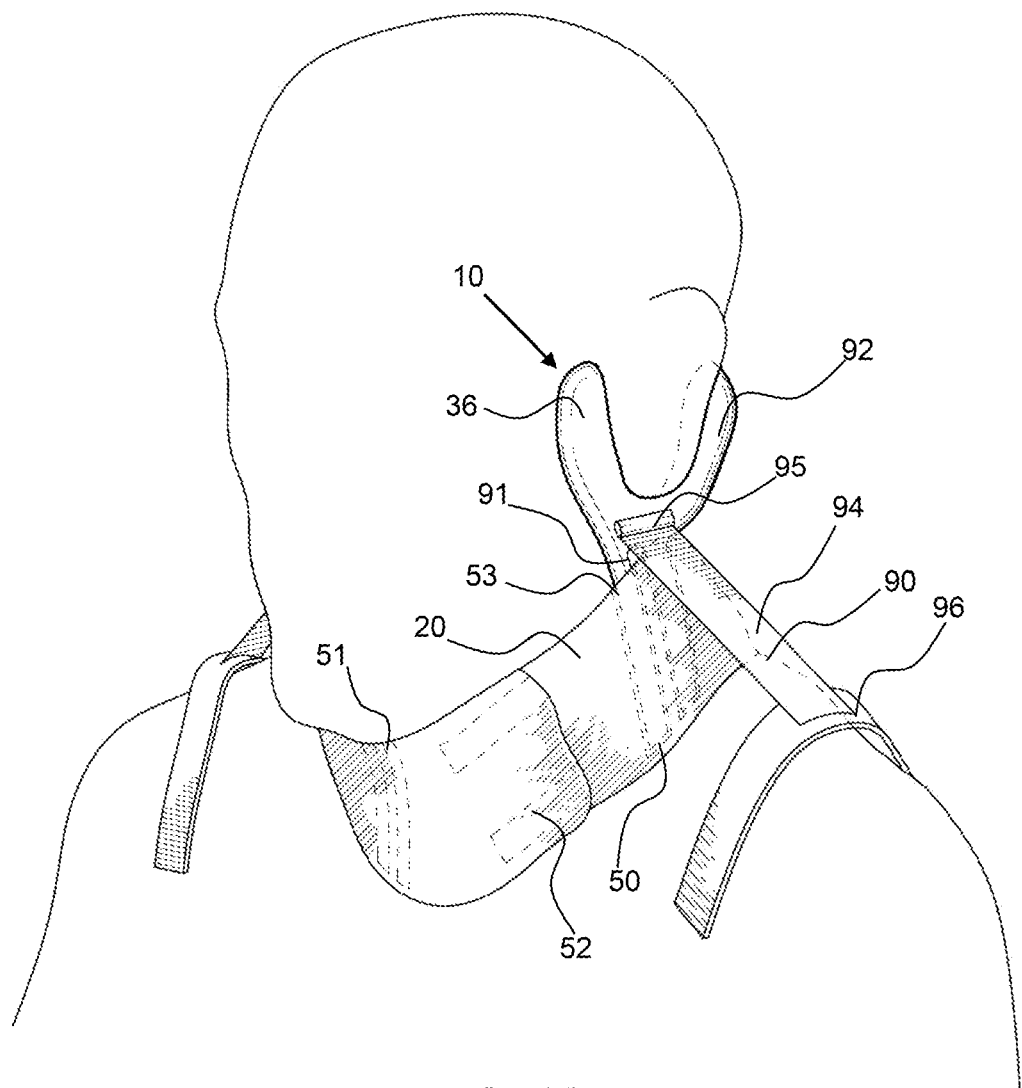
FIG. 18 shows a perspective view of an exemplary heating/cooling therapy pad system and in particular the head rest coupled with a neck therapy pad having a head rest insert configured into the head rest receiver of the neck therapy pad and a shoulder extension extending to a shoulder support.
Figure 19:
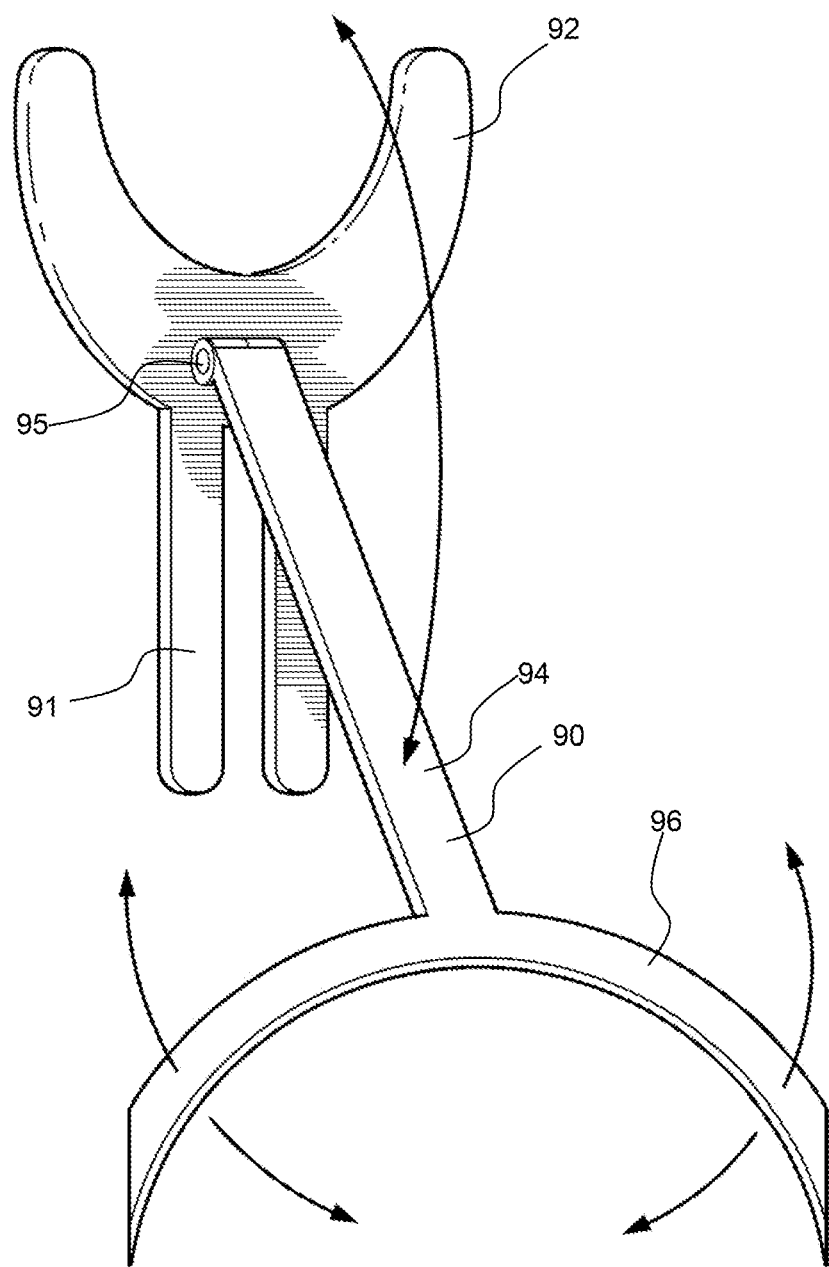
FIG. 19 shows a perspective of the head rest having a head rest insert coupled to a shoulder extension by a pivot and said shoulder extension extending to a shoulder support.

Referring now to FIGS. 18 and 19, an exemplary heating/cooling therapy pad system 10 comprise an exemplary neck therapy pad 50 that has a head rest 90 detachably attached. The head rest has a head rest pad 92, which may include a thermal medium 36 to enable the head rest pad to be heated or cooled. A head rest insert 91 extends down into the head rest receiver 53 of the neck therapy pad. A shoulder extension 94 extends from a pivot 95 to a shoulder support 96. The pivot enables the head rest insert to be inserted into the head rest receiver with the shoulder extension pivoted up and away from the shoulder. The shoulder extension and shoulder support can then be lowered down over the shoulder. As shown in FIG. 19, the shoulder support may be U-shaped and flex open to extend around and over a person's shoulder.

Figure 20:
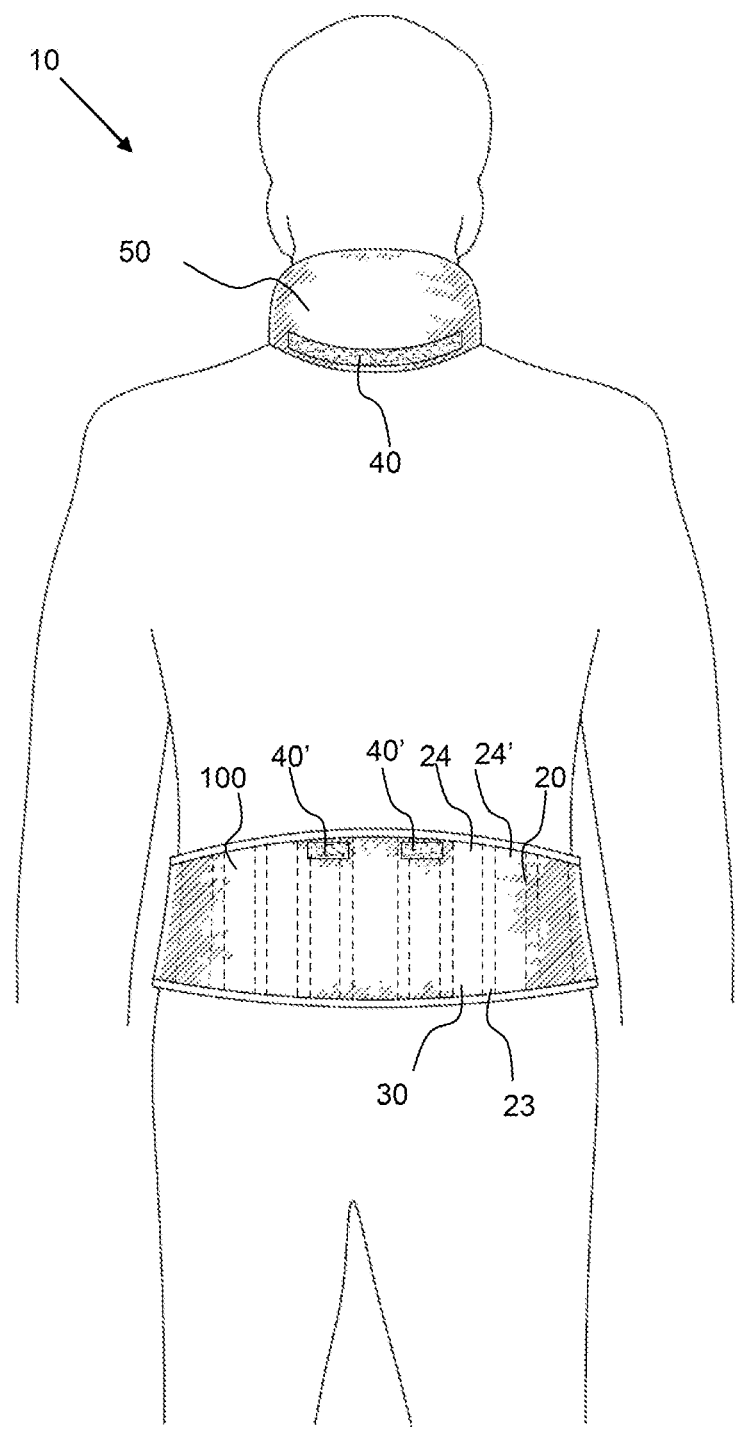
FIG. 20 shows a perspective of an exemplary lumbar therapy pad attached to a user's lumbar, or lower back region.
Figure 21:
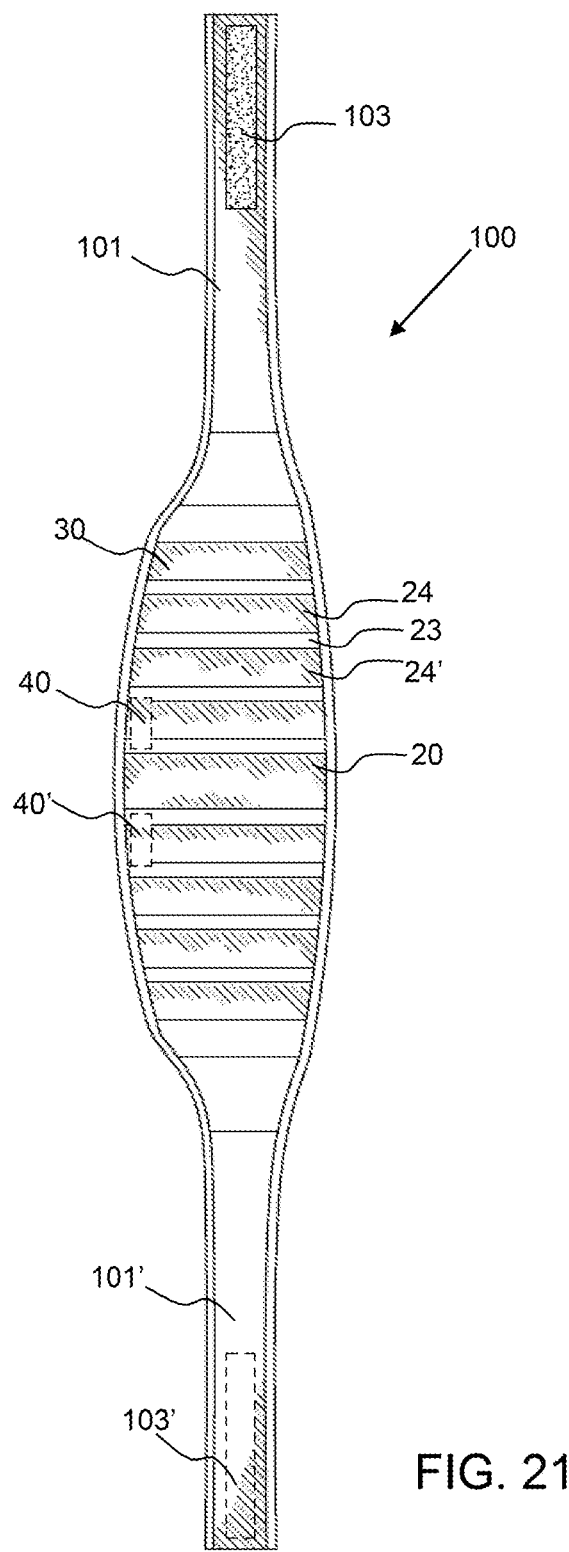
FIG. 21 shows an inside view of an exemplary lumbar therapy pad.

Referring now to FIGS. 20 and 21, an exemplary lumbar therapy pad 100 is attached to a user's lumbar, or lower back region and comprises a plurality of insert pouches 24, 24' with pouch gaps 23 therebetween for receiving thermal inserts 30. The lumbar therapy pad 100 has connectors 40, 40' for detachably attaching a spine therapy pad thereto. As shown in FIG. 21, an exemplary lumbar therapy pad has extensions 101, 101' with attachments 103, 103', respective configured thereon for detachably attaching the lumbar therapy pad around a person.

Figure 22:
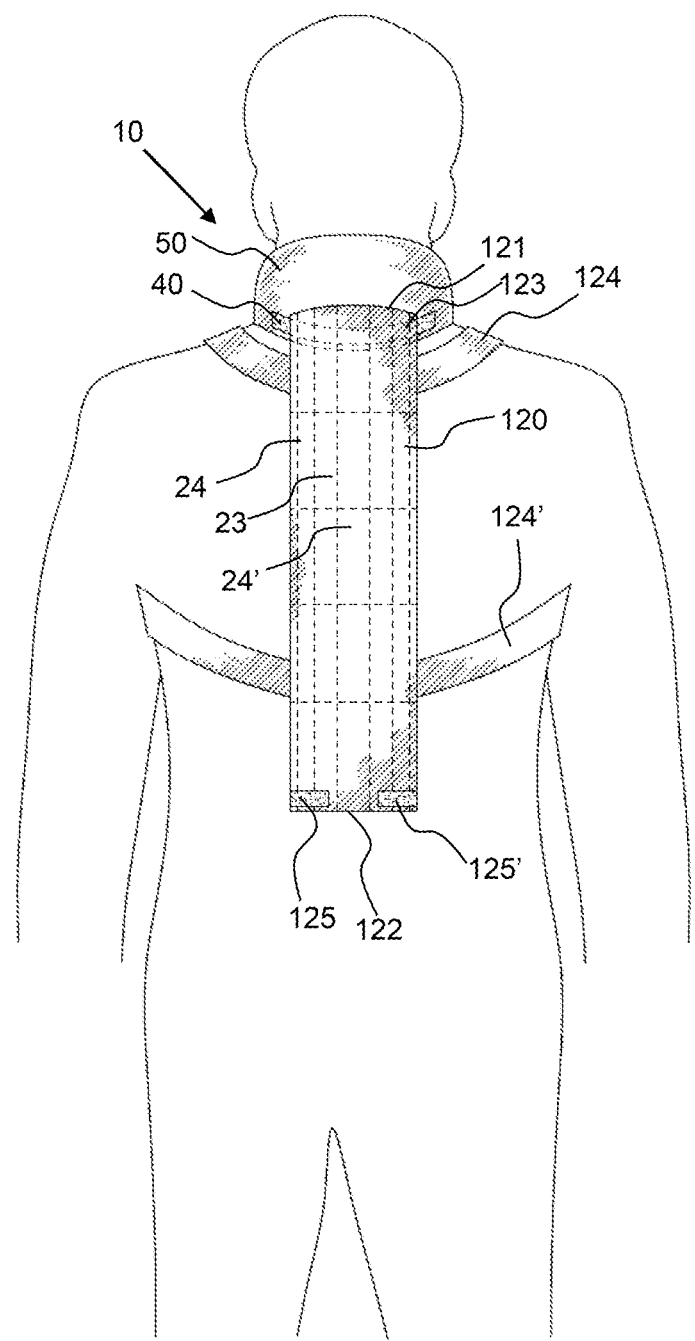
FIG. 22 shows a perspective view of an exemplary heating/cooling therapy pad system and in particular an exemplary spine therapy pad attached to a user's back spinal region.
Figure 23:
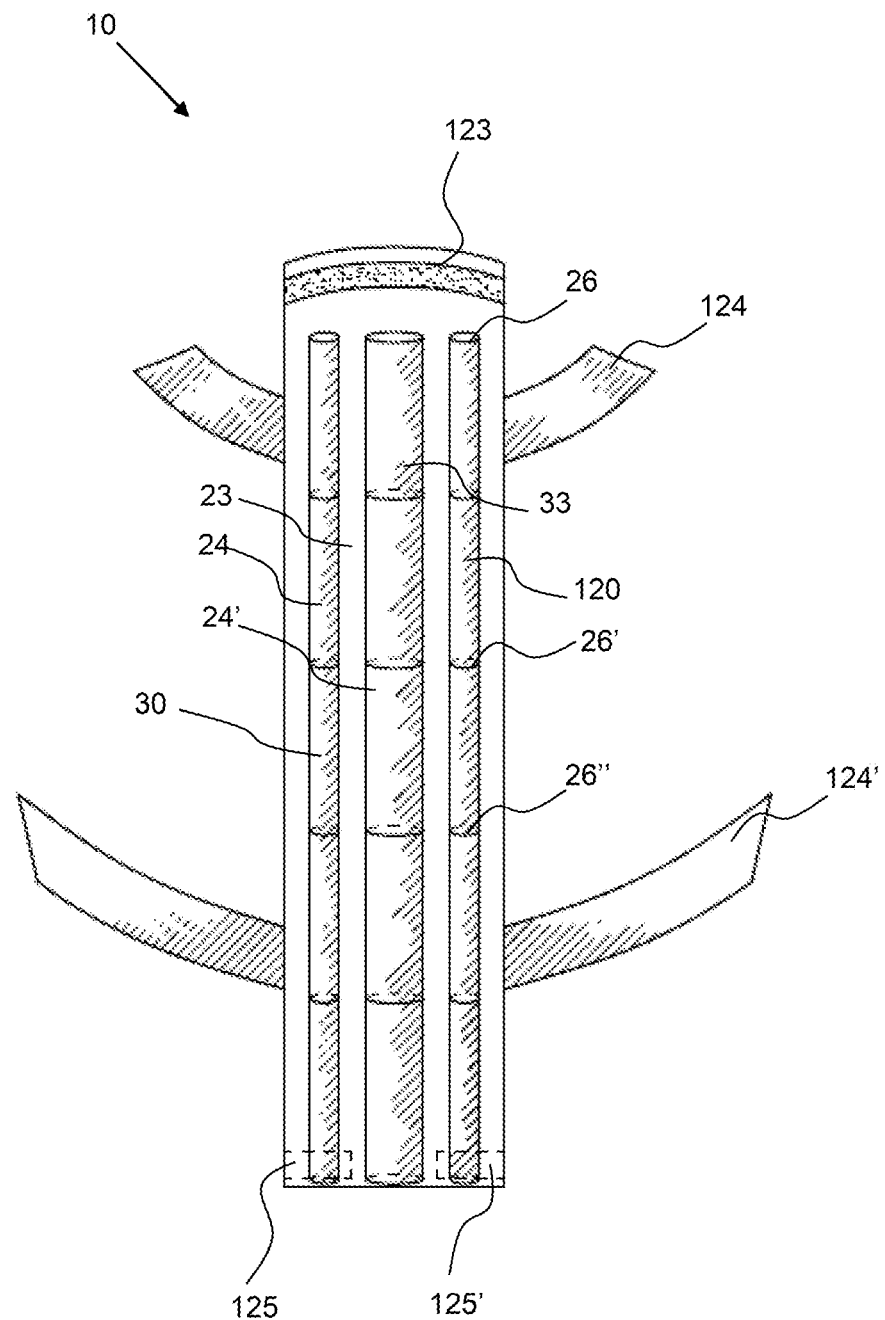
FIG. 23 shows a perspective view of the inside of an exemplary spine heat therapy pad with three vertical cylindrical shaped thermal insert rods including a large center thermal insert rod and smaller thermal insert rods on each side.

Referring now to FIGS. 22 to 25, an exemplary heating/cooling therapy pad system 10 comprise an exemplary spine therapy pad 120 configured for detachable attachment to a neck therapy pad. As shown in FIG. 22, the spine therapy pad is coupled to the connector 40 of the neck therapy pad and extends down along the person's back spinal region. The spine therapy pad has a length from a neck end 121, configured to couple to the neck therapy pad, to a lumbar end 122, configured to couple with a lumbar therapy pad or a therapy pad vest. A pair of straps 124, 124' may be used to further secure the spine therapy pad to the person. The exemplary spine therapy pad 120 comprises a plurality of insert pouches 24, 24' with pouch gaps 23 therebetween for receiving thermal inserts 30. As shown in FIG. 23, the spine therapy pad has a neck connector 123 configured to detachably attach to the connector of the neck therapy pad and lumbar connectors 125, 125' configured to detachably attach to connectors of a lumbar therapy pad or therapy pad vest.

As shown in FIG. 23, a centrally located thermal insert 24', a spinal thermal insert, may be larger in diameter than the thermal inserts 24 adjacent thereto. This larger diameter thermal insert along the center is configured for providing good contact with the center recess along a person's back, corresponding with the spine. This spinal thermal insert may be about 50% larger in diameter or more than the adjacent thermal inserts, or about 75% larger in diameter or more than the adjacent thermal inserts, or about 100% larger in diameter or more than the adjacent thermal inserts. In an exemplary embodiment, the spinal thermal insert is a thermal insert rod 33 and the adjacent thermal inserts are not, and may be rectangular in shape. The thermal inserts shown in FIG. 23 extend vertically along the length of the spine therapy pad from the top connector 123 to the bottom connectors 125, 125'. The exemplary spine therapy pad 120 may have a single pouch opening 26 configured to receive an elongated thermal insert rod that extends down along the length of the pouch or may have a plurality of pouches and separate pouch openings 26-26'' to allow a user to insert the thermal inserts 30 in a desired location along the length of the exemplary spine therapy pad. An exemplary spine therapy pad 120 may have two or more pouch openings along the length, three or more, four or more, five or more, six or more and any range between and including the numbers provided. As shown, there are five thermal insert rods configured in series along the length of exemplary spine therapy pad.

Figure 24:
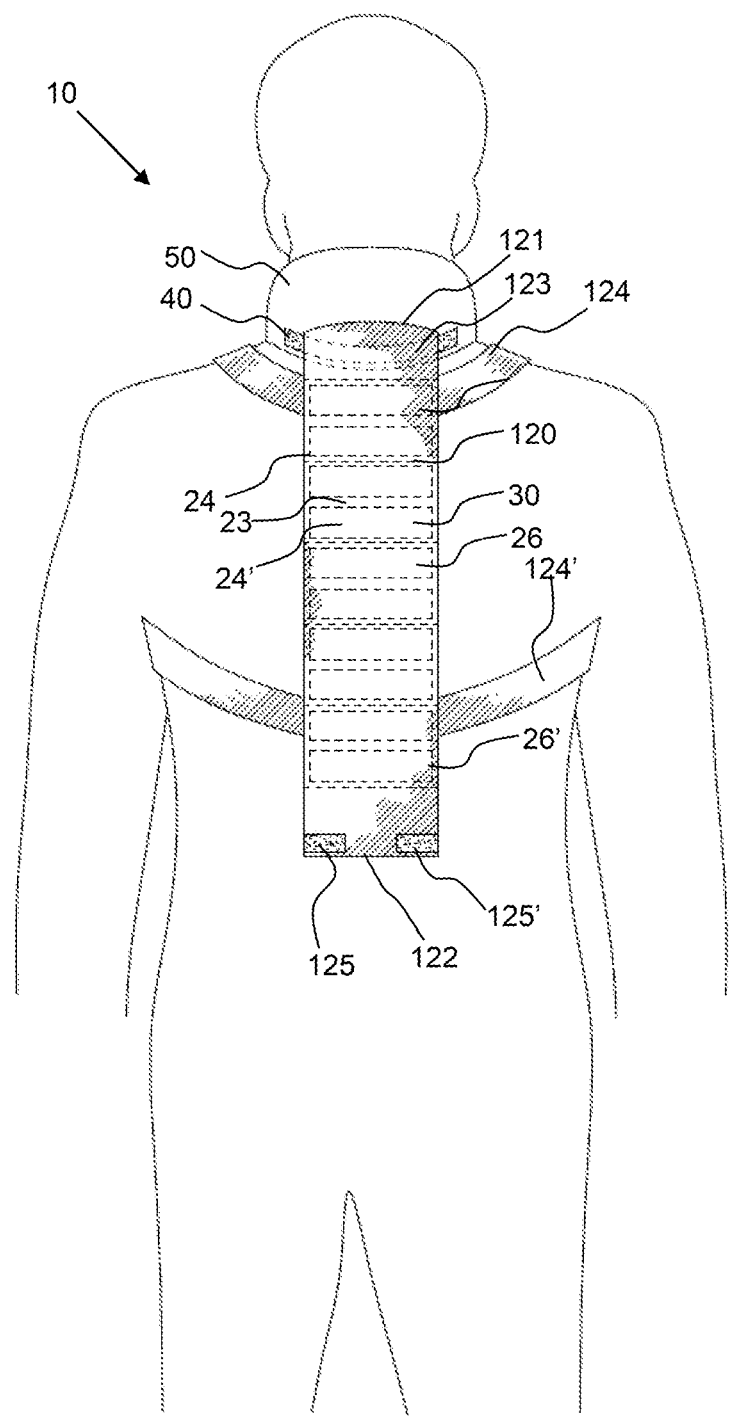
FIG. 24 shows a perspective view of a heating/cooling therapy pad system and in particular the spine therapy pad with horizontal thermal inserts attached over a user's spinal region by a detachable attachment to a neck therapy pad.
Figure 25:
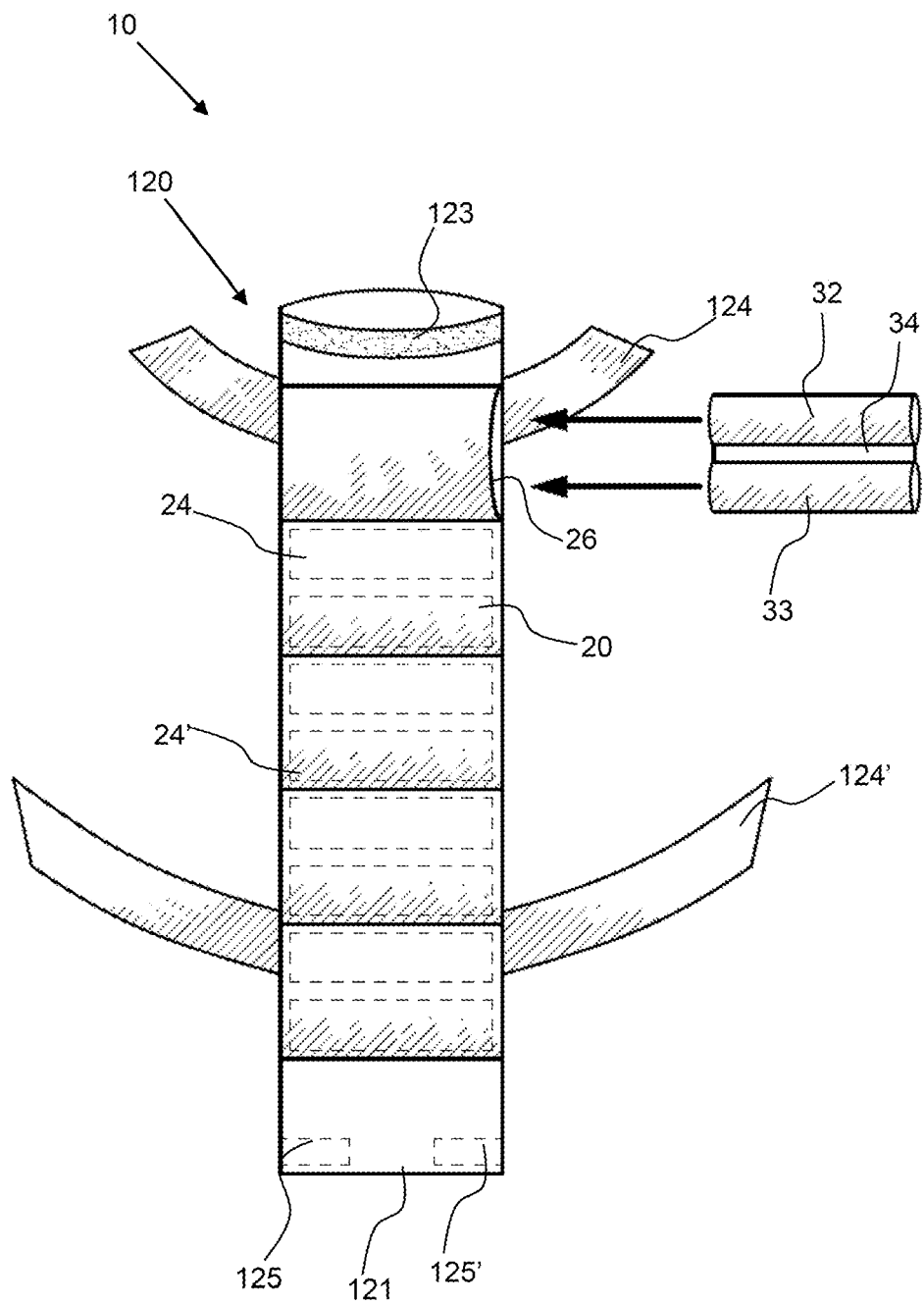
FIG. 25 shows a perspective view of the inside of an exemplary spine therapy pad having a dual tube thermal insert configured for inserting into a thermal insert pouch.

As shown in FIG. 24, an exemplary spine therapy pad 120 is configured with horizontal thermal inserts 30, or inserts that extend into the spine therapy pad along a direction orthogonal to the length of the spine therapy pad. As shown in FIG. 25, a thermal insert 30 may be a dual thermal insert 32 comprising two thermal insert rods 33. The pouch opening may extend along the length of the spine therapy pad. Each horizontally oriented thermal insert 30 may have a individual pouch opening 26, 26'.

Figure 26:
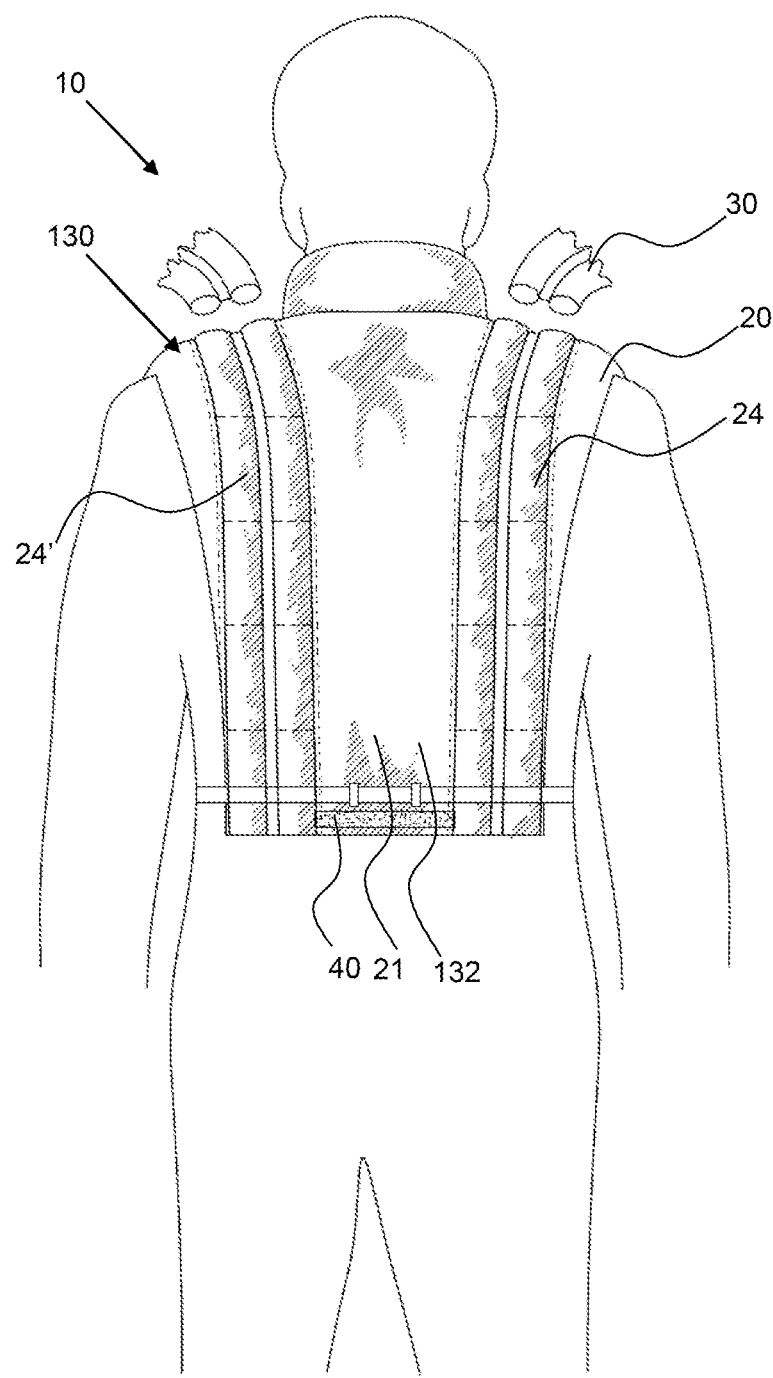
FIG. 26 shows a perspective view of a heating/cooling therapy pad system and in particular the vest therapy pad attached over a user's back and shoulders.
Figure 27:
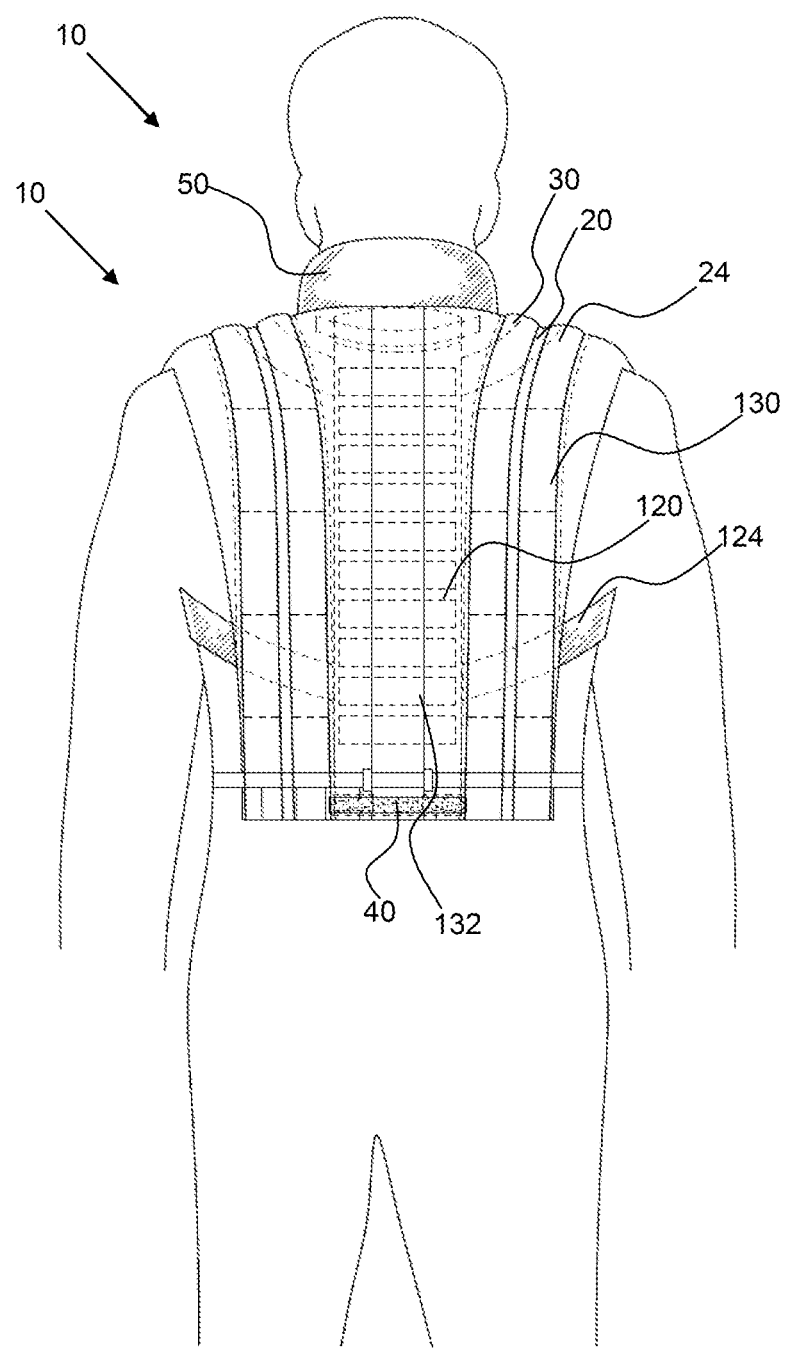
FIG. 27 shows a perspective view of a heating/cooling therapy pad system and in particular an exemplary vest therapy pad configured over a user's shoulder and back region with the non-overlapping spine therapy pad configured thereunder; as indicated by the dashed lines.
Figure 28:
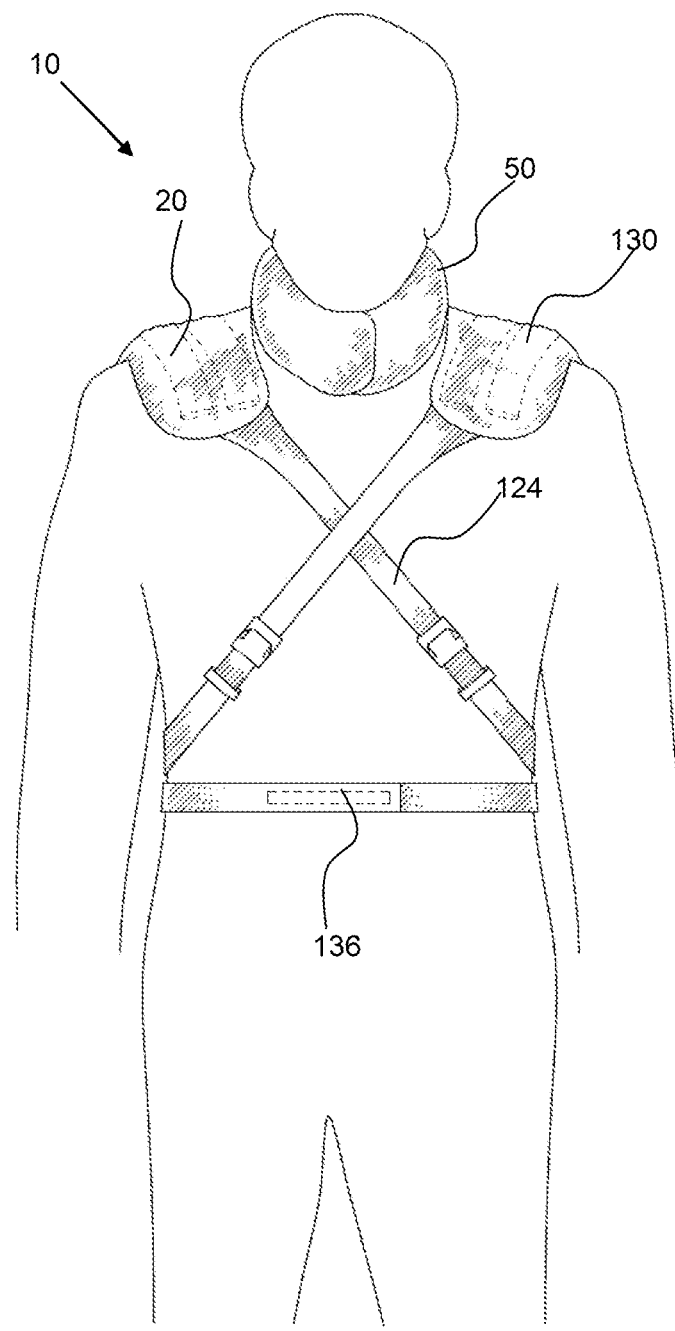
FIG. 28 shows a perspective view of an exemplary vest therapy pad overlaying a user's body with straps and fasteners across the user's front torso.

Referring now to FIGS. 26 to 28, an exemplary heating/cooling therapy pad system 10 comprise an exemplary vest therapy pad 130 attached over a user's back and shoulders. The vest therapy pad has insert pouches 24 for receiving thermal inserts 30. The vest therapy pad may include a connector 40 for coupling with a spine therapy pad. Also, a vest therapy pad may have spine receiving portion 132, or an area between the thermal insert pouches 24, 24' that is void of thermal inserts or pouches. This area may be open or may only comprise a connector fabric, such as the outer covering 21 of the thermal therapy pad 20. As shown in FIG. 27, an exemplary vest therapy pad 130 is configured over a user's shoulder and back region with the spine therapy pad 120 configured in the spine receiving portion, thereunder; as indicated by the dashed lines. The vest may have one or more straps 124 for securing the vest therapy pad to a person.

Figure 29:
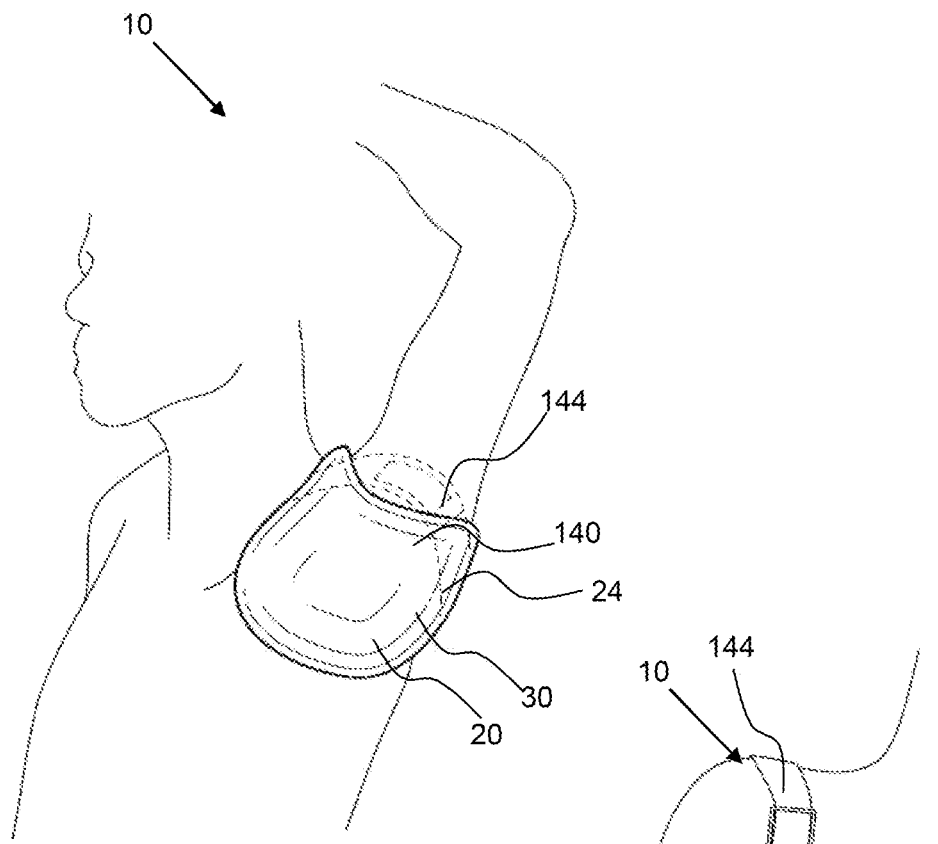
FIG. 29 shows a perspective view of an exemplary armpit therapy pad attached to a user's body by a strap with the user's arm raised.
Figure 30:
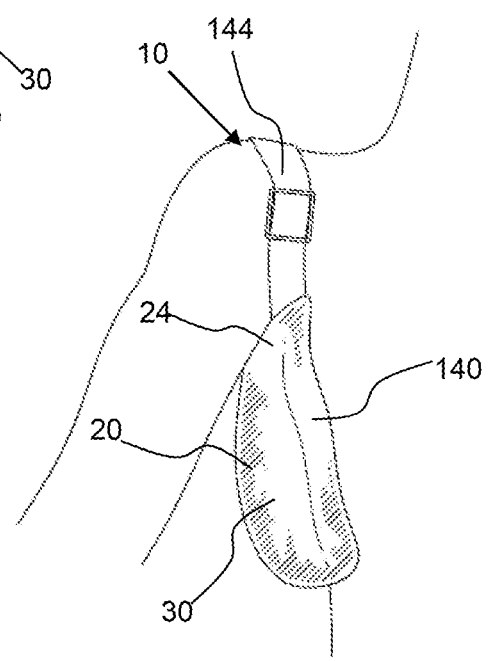
FIG. 30 shows a perspective view of an exemplary armpit therapy pad attached to a user's body by a strap with the user's arm lowered.

Referring now to FIGS. 29 and 30, an exemplary armpit therapy pad 140 is attached to a user's body by a strap 144. The armpit therapy pad 140 may include an insert pouch 24 for receiving a thermal insert 30.

Figures 31, 32:
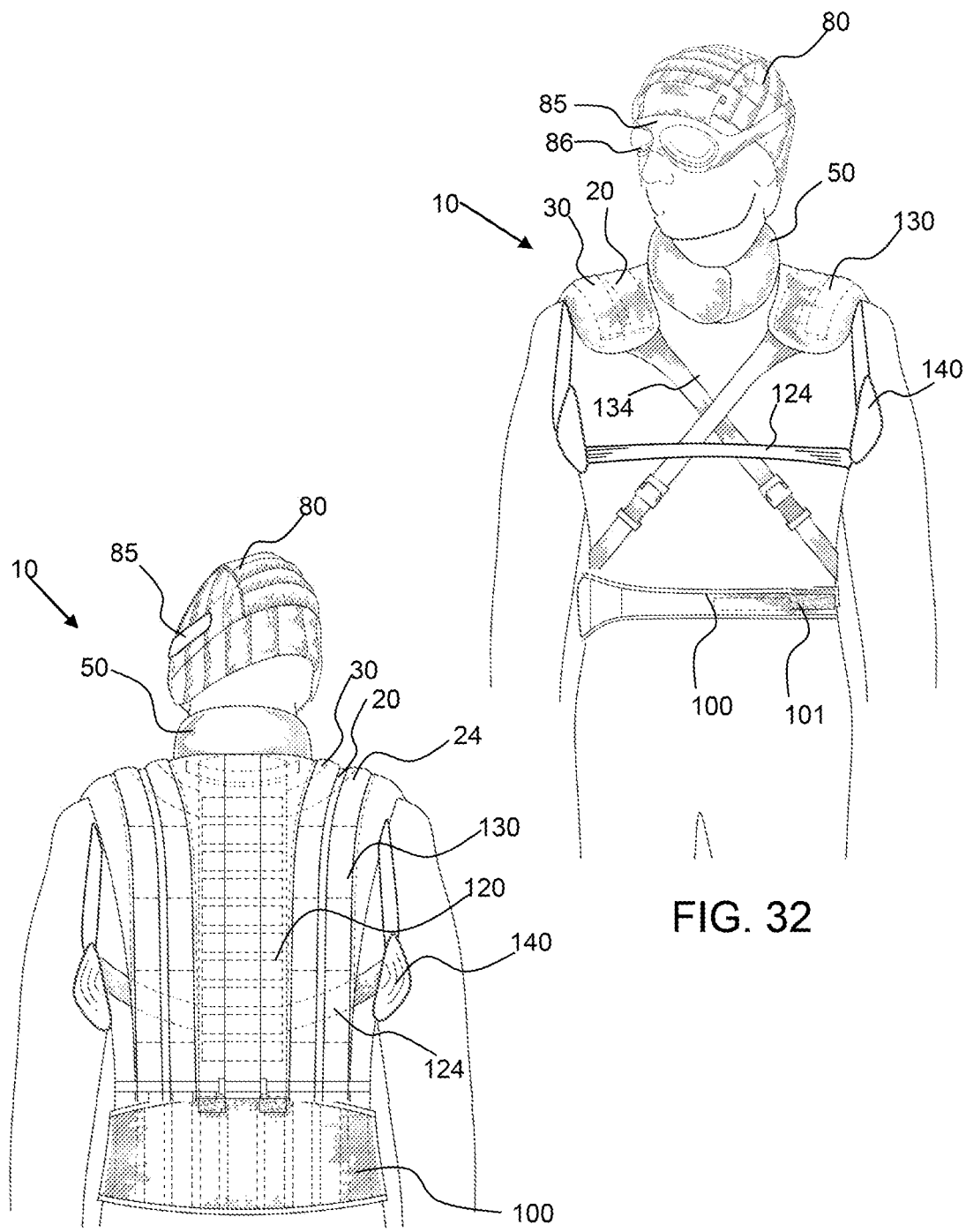
FIG. 31 shows a back view of a person donning an exemplary heating/cooling therapy pad system comprising a plurality of thermal therapy pads including a head therapy pad with a face therapy pad attached, a neck thermal therapy pad, a spine thermal therapy pad, a lumbar thermal therapy pad, an armpit thermal therapy pad and a thermal therapy pad vest.
FIG. 32 shows a front view of the person donning an exemplary heating/cooling therapy pad system shown in FIG. 31, wherein the heating/cooling therapy pad system comprises a plurality of thermal therapy pads including a head therapy pad with a face therapy pad attached, a neck thermal therapy pad, a spine thermal therapy pad, a lumbar thermal therapy pad, an armpit thermal therapy pad and a thermal therapy pad vest.

Referring now to FIGS. 31 and 32, shows front and back views of a person donning an exemplary heating/cooling therapy pad system 10 having a plurality of thermal therapy pads 20 including a head therapy pad 80 with a face therapy pad 85, having a face thermal insert, detachably attached, a neck thermal therapy pad 50, a spine thermal therapy pad 120, a lumbar thermal therapy pad 100 and a thermal therapy pad vest 130. Note that each of the components shown are more fully described and shown in the proceeding figures. Also note that the chin rest 70, as shown in FIGS. 10 to 12 may also be used with this integrated system. Also, the head rest 90, as shown in FIGS. 18 and 19 may be used with this integrated system and secured to the neck thermal therapy pad. The entire heating/cooling therapy pad system, or portions thereof, may be used to treat people suffering from heat injuries, such as heat exhaustion and/or heat stroke, as the thermal therapy pads are configured over parts of the body that can effectuate rapid cooling.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A heating/cooling therapy pad system comprising:
a) a thermal therapy pad comprising:
   i) an outer covering;
   ii) a thermal insert comprising a thermal medium;
   iii) a plurality of insert pouches, each configured for receiving and retaining a thermal insert;
   iv) a pouch gap between adjacent insert pouches; and
b) a connector configured on the thermal pad for connecting with a second thermal pad thereto;
c) a neck therapy pad having extensions for extending around a person's neck and an attachment on each of the extensions to detachably attach the extensions together
d) chin rest comprising:
   i) a chin rest pad; and
   ii) a chin rest insert;
wherein the neck therapy pad comprises a chin rest receiver for receiving and retaining the chin rest insert, wherein the chin rest is configured to support a person's chin;
e) a head rest comprising:
   i) a head rest insert;
   ii) a head rest pad coupled to the head rest insert;
   iii) a shoulder extension coupled to the head rest insert;
   iv) a shoulder support coupled to the shoulder extension and configured to rest on a Person's shoulder; and
wherein the neck therapy pad comprises a head rest receiver for receiving and retaining the head rest insert, wherein the head rest is configured to support a person's head.

2. The heating/cooling therapy pad system of claim 1, wherein the thermal insert is a thermal insert rod having a cylindrical shape.

3. The heating/cooling therapy pad system of claim 1, wherein the pouch gap is at least 25% of the width of the thermal insert.

4. The heating/cooling therapy pad system of claim 1, further comprising a hygiene cover that is coupled to the connector and extends along an inside surface of the neck therapy pad.

5. The heating/cooling therapy pad system of claim 1, wherein the neck therapy pad comprises
a thermal pad portion configured between the extensions;
wherein the thermal pad portion has a neck extension centrally located along the thermal pad portion and having a neck extension length that is greater than the length of the thermal pad portion proximal to the extensions.

6. The heating/cooling therapy pad system of claim 5, wherein the thermal pad portion is curved having an arc shape across a top of the thermal pad portion.

7. The heating/cooling therapy pad system of claim 1, wherein the therapy pad system comprises an armpit therapy pad having extensions for extending around the shoulder and an attachment on each of the extensions to detachably attach the extensions together.

8. A heating/cooling therapy pad system of claim 1, further comprising:
a) a thermal therapy pad comprising:

i) an outer covering;
ii) a thermal insert comprising a thermal medium;
iii) a plurality of insert pouches, each configured for receiving and retaining a thermal insert;
i) a pouch gap between adjacent insert pouches; and
b) a connector configured on the thermal pad for connecting with a second thermal pad thereto;
c) a neck therapy pad having extensions for extending around a person's neck and an attachment on each of the extensions to detachably attach the extensions together;
d) a head rest comprising:
i) a head rest insert;
ii) a head rest pad coupled to the head rest insert;
iii) a shoulder extension coupled to the head rest insert;
iv) a shoulder support coupled to the shoulder extension and configured to rest on a person's shoulder;
wherein the neck therapy pad comprises a head rest receiver for receiving and retaining the head rest insert, wherein the head rest is configured to support a person's head;
wherein the therapy pad system comprises a neck therapy pad having extensions for extending around a person's neck and an attachment on each of the extensions to detachably attach the extensions together.

9. The heating/cooling therapy pad system of claim 8, wherein the head rest pad is U-shaped to extend around a person's ear.

10. The heating/cooling therapy pad system of claim 8, wherein the head rest pad comprises thermal medium.

11. The heating/cooling therapy pad system of claim 8, wherein the head rest further comprises a pivot configured between the shoulder extension and the head rest insert to allow the insert to pivot with respect to the shoulder extension.

12. The heating/cooling therapy pad system of claim 8, wherein the therapy pad system comprises a spine therapy pad comprising:

a) a neck end;
b) a lumbar end;
c) a length from the neck end to the lumbar end;
d) a neck connector configured proximal to the neck end and configure to detachably attach to the connector configured on the neck therapy pad
e) a lumbar connector configured proximal to the lumbar end.

13. The heating/cooling therapy pad system of claim 12, wherein the plurality of pouches of the spine therapy pad extend orthogonally to the length of the spine therapy pad.

14. The heating/cooling therapy pad system of claim 12, wherein the therapy pad system further comprises a spine therapy pad and a lumbar therapy pad, said lumbar therapy pad comprising:

a) extensions for extending around a lumbar and torso of a person; and
b) an attachment on each of the extensions to detachably attach the extensions together;
c) a connector for coupling with a lumbar attachment of the spine therapy pad.

15. The heating/cooling therapy pad system of claim 8, wherein the therapy pad system comprises a head therapy pad that is dome shaped and configured to fit over a person's head.

16. The heating/cooling therapy pad system of claim 15, wherein the head therapy pad is elastic wherein the outer covering is an elastic material.

17. The heating/cooling therapy pad system of claim 15, wherein the therapy pad system further comprises a face therapy pad having a face thermal insert.

18. The heating/cooling therapy pad system of claim 17, wherein the face thermal insert is detachably attachable to the face therapy pad and comprises eye thermal portions.

* * * * *